United States Patent [19]

Farbood et al.

[11] Patent Number: 4,657,862

[45] Date of Patent: Apr. 14, 1987

[54] PREPARATION OF NATURALLY-OCCURRING C2-C5 ALKYL ESTERS OF C4-C5 CARBOXYLIC ACIDS BY MEANS OF FERMENTATION OF C5-C6 AMINO ACIDS IN THE PRESENCE OF C2-C5 ALCOHOLS

[75] Inventors: Mohamad I. Farbood, Holmdel; James A. Morris, Belmar; Eugene W. Seitz, Middletown, all of N.J.

[73] Assignee: International Flavors & Fragrances Inc., New York, N.Y.

[21] Appl. No.: 636,225

[22] Filed: Jul. 31, 1984

[51] Int. Cl.$^4$ .................... C12P 7/62; C12P 7/40; C12P 7/52; C12N 1/14
[52] U.S. Cl. .................... 435/135; 435/136; 435/141; 435/254
[58] Field of Search ............ 435/135, 136, 171, 254, 435/911, 141

[56] References Cited

U.S. PATENT DOCUMENTS

| | | | |
|---|---|---|---|
| 953,025 | 3/1910 | Effront | 435/136 |
| 1,866,568 | 7/1932 | Iszak et al. | 435/135 |
| 3,409,506 | 11/1968 | Stevens | 435/116 |
| 4,451,565 | 5/1984 | Gatfield et al. | 435/117 |
| 4,487,832 | 12/1984 | Heady et al. | 435/135 |
| 4,560,656 | 12/1985 | Farbood et al. | 435/136 |

FOREIGN PATENT DOCUMENTS

0018333 10/1980 European Pat. Off. .
59-227291 12/1984 Japan .
83/01072 3/1983 PCT Int'l Appl. .

OTHER PUBLICATIONS

Lanza, et al., "Aroma Production by Cultures of Ceratocystis Moniliformis", *J. Agr. Food Chem.*, vol. 24(6), 1976, pp. 1247-1250.

Ruben et al., (1978), vol. 14(6), pp. 849-856, "The Exolipase Biosynthesis by *Oosprora Fragrans*", Prikladnaja Biokhimiia i Mikrobiologiia.

Chem. Abstracts, vol. 72, 1970, 20589p (Abstract of Petrosyan Vinodel, Vinograd, SSSR) 1969, 29(6), 11-13.

Chem. Abstracts, vol. 100, 1984, 207827d (Abstract of Ikemi, et al. Nippon Jozo Kyokai Zasshi, 79(2) 119-123.

Kiyoshi Nakayama "Microorganisms In Amino Acid Fermentation", Proc. IV, IFS:Ferment. Techonl., Today 433-438 (1972).

The Merck Index, 10th Edition, Published by Merck & Company, Rahway, New Jersey, 1983, p. 265, at Monograph 1879, "Castor Oil".

Chem. Abstracts, vol. 94:63793x, Brodelius, et al., Abstract of European Application 18,333 cited, supra as reference AM.

Chem. Abstracts, vol. 67:10364u (Rodopulo, et al.).

Chem. Abstracts, vol. 94:14020j, Abstract of Japanese Published Application 79/154592, published on 12/5/79.

*Primary Examiner*—Charles F. Warren
*Assistant Examiner*—John E. Tarcza
*Attorney, Agent, or Firm*—Arthur L. Liberman

[57] ABSTRACT

Described is a process for the preparation of $C_2$–$C_5$ alkyl esters of $C_4$–$C_5$ carboxylic acids defined according to the structure:

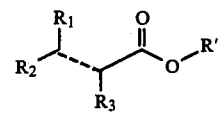

by means of fermentation of one or more $C_5$–$C_6$ amino acids defined according to the structure:

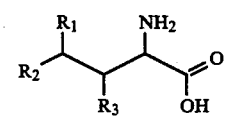

in the presence of a $C_2$–$C_5$ alcohol according to the reaction:

(Abstract continued on next page.)

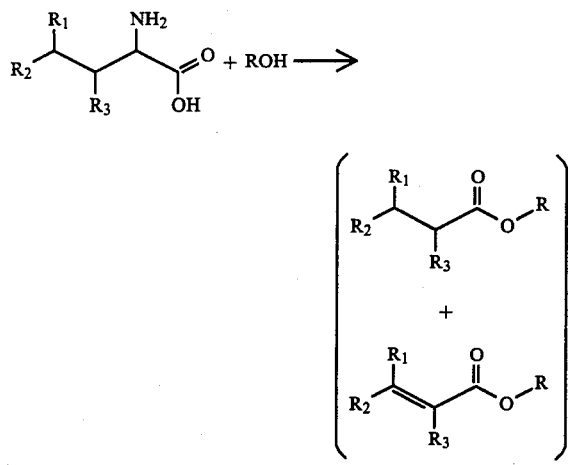

-continued wherein $R_1$, $R_2$ and $R_3$ each represent hydrogen or methyl with the proviso that at least one of $R_1$, $R_2$ and $R_3$ represents methyl and wherein R represents $C_2$–$C_5$ alkyl and wherein R is the same as R'. Also described are the products produced according to such process as well as their organoleptic utilities for augmenting or enhancing the aroma or taste of consumable materials selected from the group consisting of perfume compositions, colognes, perfumed articles, foodstuffs, chewing gums, medicinal products, toothpaste, chewing tobaccos and smoking tobaccos.

8 Claims, 14 Drawing Figures

GLC PROFILE FOR EXAMPLE II.

GC-MS SPECTRUM FOR EXAMPLE II.

GC-MS SPECTRUM FOR EXAMPLE II.

GLC PROFILE FOR FIRST TRAP OF EXAMPLE III.

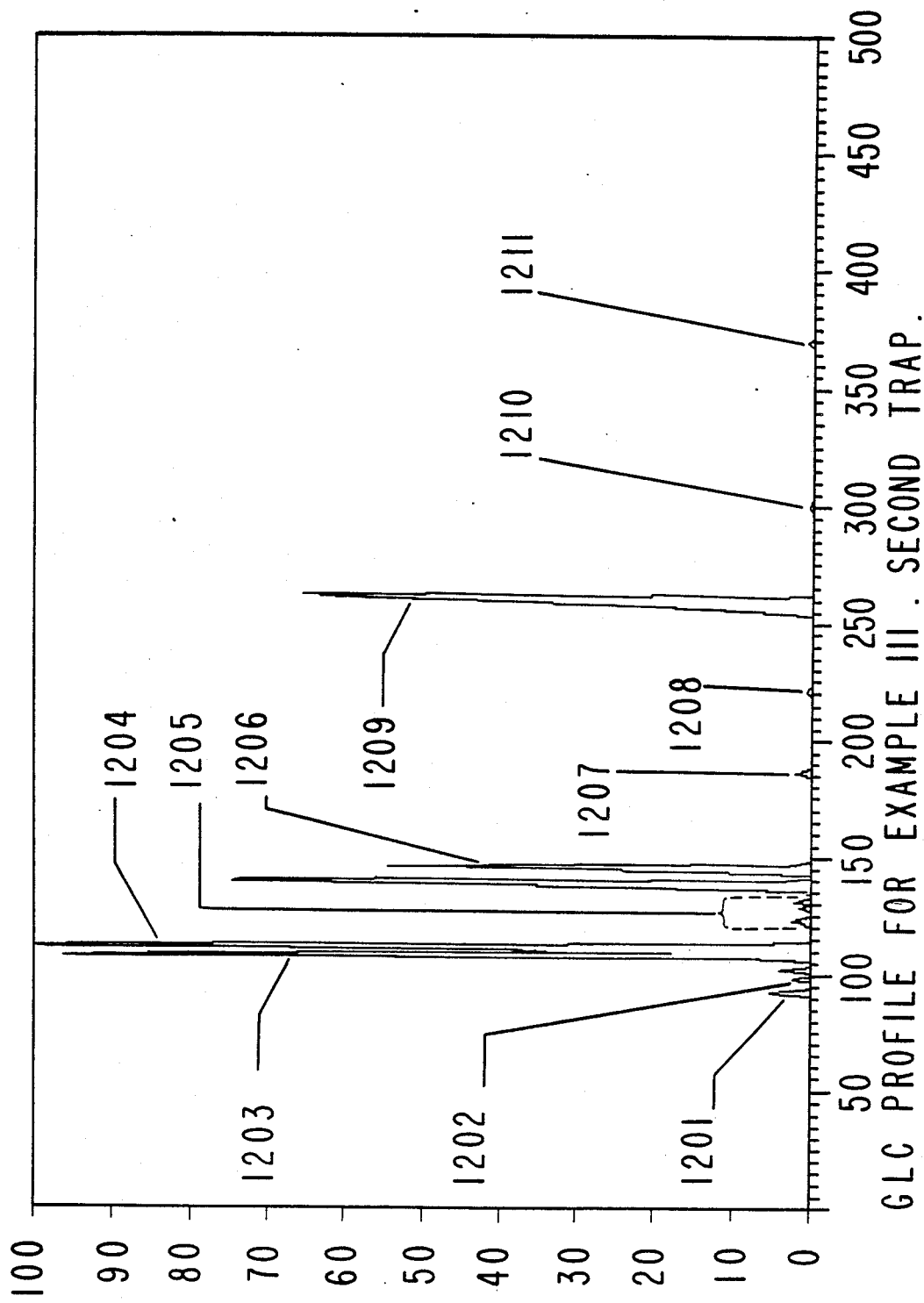

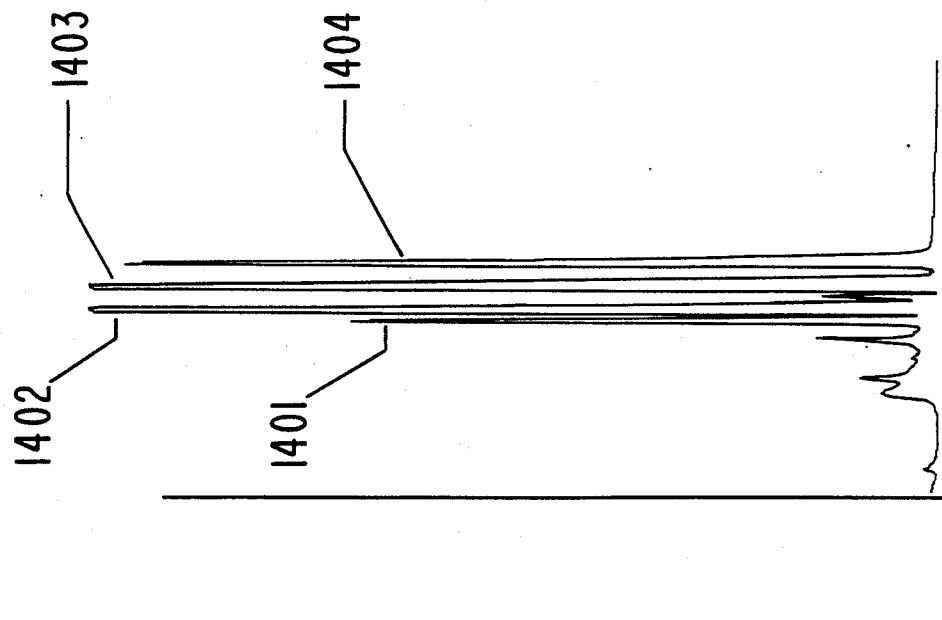
FIG. 14 — GLC PROFILE FOR EXAMPLE IX.
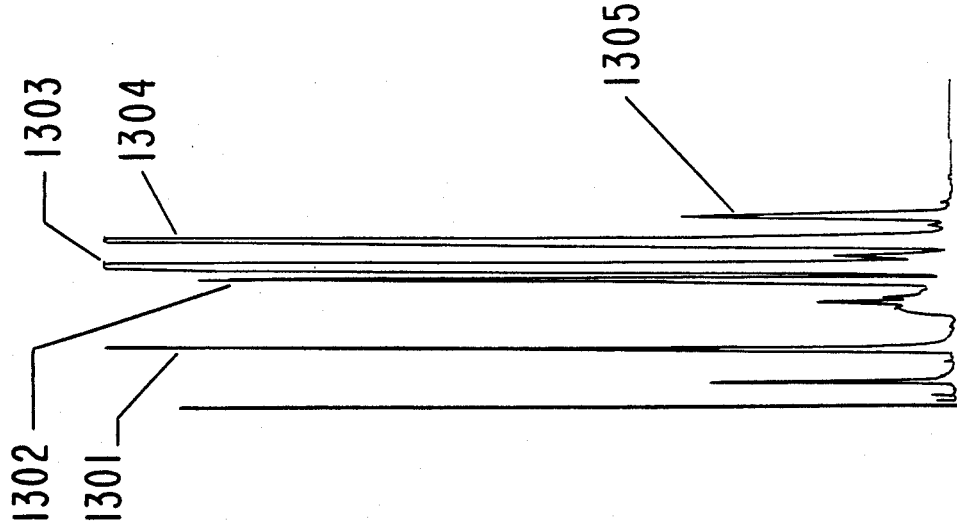
FIG. 13 — GLC PROFILE FOR EXAMPLE VIII.

PREPARATION OF NATURALLY-OCCURRING C2-C5 ALKYL ESTERS OF C4-C5 CARBOXYLIC ACIDS BY MEANS OF FERMENTATION OF C5-C6 AMINO ACIDS IN THE PRESENCE OF C2-C5 ALCOHOLS

BACKGROUND OF THE INVENTION

The present invention relates to a process for the microbial synthesis of esters from acids.

A process for the preparation of enzyme-mediated synthesis of esters and lactones is set forth in U.S. Pat. No. 4,451,565 issued on May 29, 1984 whereby the enzyme assisted reaction:

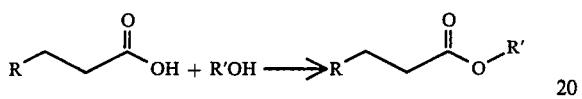

is disclosed. In the reaction of U.S. Pat. No. 4,451,565, R represents a hydrogen atom or a straight chain or branched saturated or unsaturated hydrocarbon radical which has 1 to 21 carbon atoms and which optionally can be substituted by hydroxyl groups or alkoxy groups with 1 to 10 carbon atoms. R' represents $C_1$–$C_{15}$ primary or secondary alkyl.

A process for the preparation of terpene alcohol esters by the reaction of terpene alcohols with fatty acids in the presence of selected lipases is described in Japanese Patent Application No. 54/041838. Rodopulo, et al, Chemical Abstracts, Volume 67, 1967, at abstract 10364u (abstract of Vinodel. -inograd. SSSR 27(3), 15–20 (1967) discloses, in wine fermentation, a process of oxidative deamination accompanied by the generation of alcohols, carbonic acids and ethers "important for the wine bouquet".

Brodelius, et al, European Patent Application No. 18,333 (abstracted at Chem. Abstracts, Volume 94: 63793x) discloses the deamination of methionine having the structure:

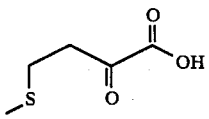

by means of the fermentation reaction:

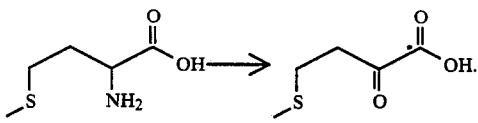

Indeed, valine, leucine and isoleucine are shown by Lehninger "Biochemistry", 1975, published by Worth Publishers, Inc. to undergo the following conversions involving:

a. α-keto-isovaleric acid in the case of valine;
b. α-keto-β-methyl-valeric acid in the case of isoleucine; and
c. α-ketoisocaproic acid in the case of leucine, thusly:

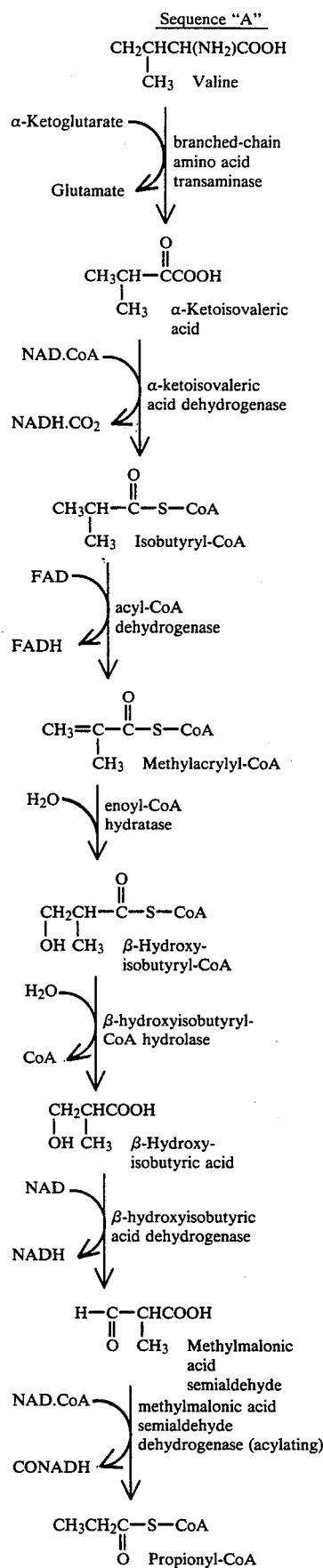

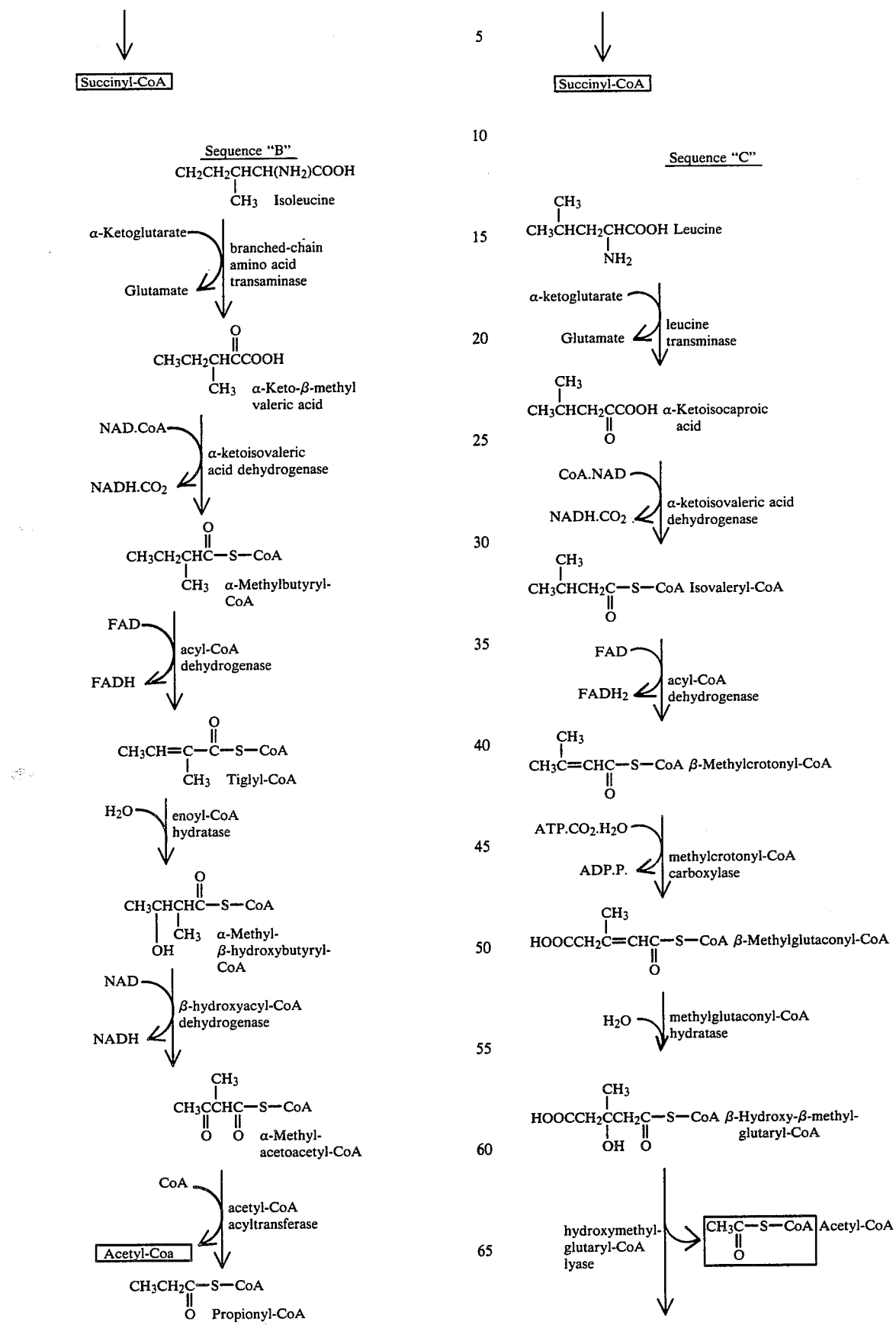

-continued
Sequence "C"

↓

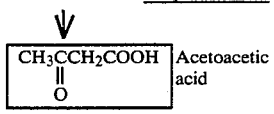
Acetoacetic acid

In the flavor and fragrance art, a need has arisen for the development and efficient production of naturally occurring carboxylic acid esters which have heretofor been found to be useful and necessary in the creation of flavor formulations used in augmenting or enhancing the aroma or taste of foodstuffs, chewing gums, toothpastes, medicinal products, chewing tobaccos and smoking tobaccos and also useful in augmenting or enhancing the aroma of perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like.

U.S. Pat. No. 953,025 issued on Mar. 29, 1910 (Effront) discloses the fermentation reaction of amino carboxylic acids using yeast as the fermentation catalyst to form carboxylic acid thusly:

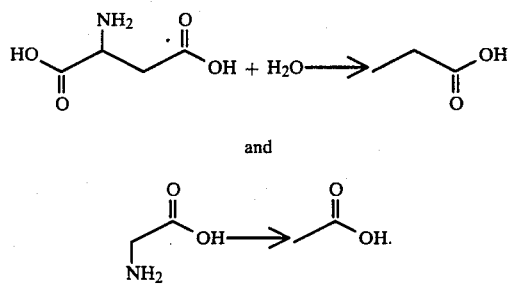

and

The "Effront" process is different, in kind, from the process of our invention.

Heretofor, nothing in the prior art discloses either explicitly or implicitly a process for the deamination of naturally occurring amino acid by means of fermentation to yield naturally occurring organoleptically useful esters.

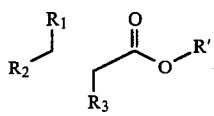

wherein $R_1$, $R_2$ and $R_3$ each represent hydrogen or methyl; wherein the dashed line represents a carbon-carbon single bond or a carbon-carbon double bond; wherein R' represents $C_2$-$C_5$ alkyl with the proviso that at least one of $R_1$, $R_2$ and $R_3$ represents methyl are trapped from the gas stream flowing from the fermentation vessel.

Figure 3:
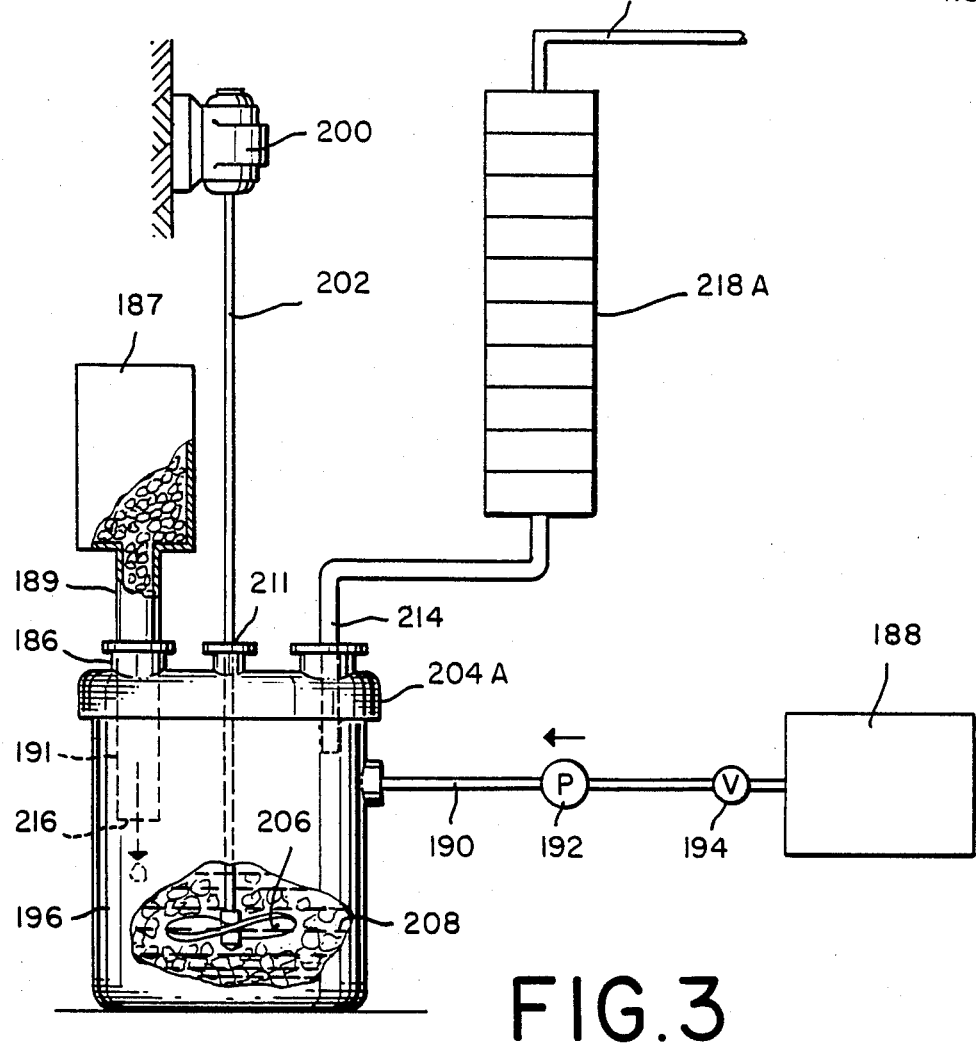

FIG. 3 is a schematic block-flow diagram of that section of the apparatus useful for effecting the process of our invention which involves the admixing of the ester-adsorbed charcoal with distillation solvent immediately prior to distillation of the ester material.

Figure 4:
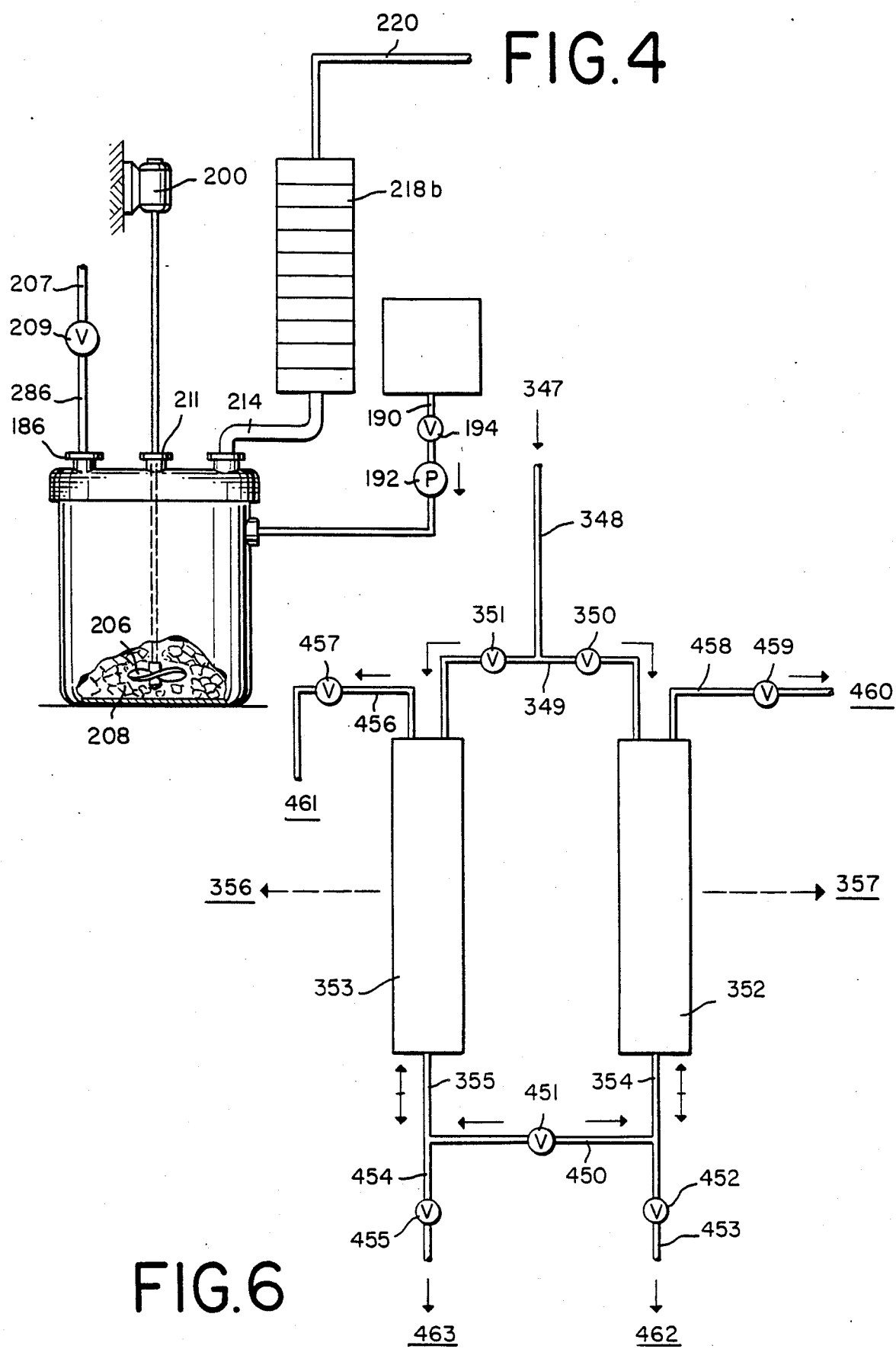

FIG. 4 is a schematic block-flow diagram of that portion of the apparatus useful in effecting the process of our invention which involves the distillation of the esters from the ester-adsorbed charcoal mixture using distillation material in order to carry out such distillation during the distillation step.

Figure 5:
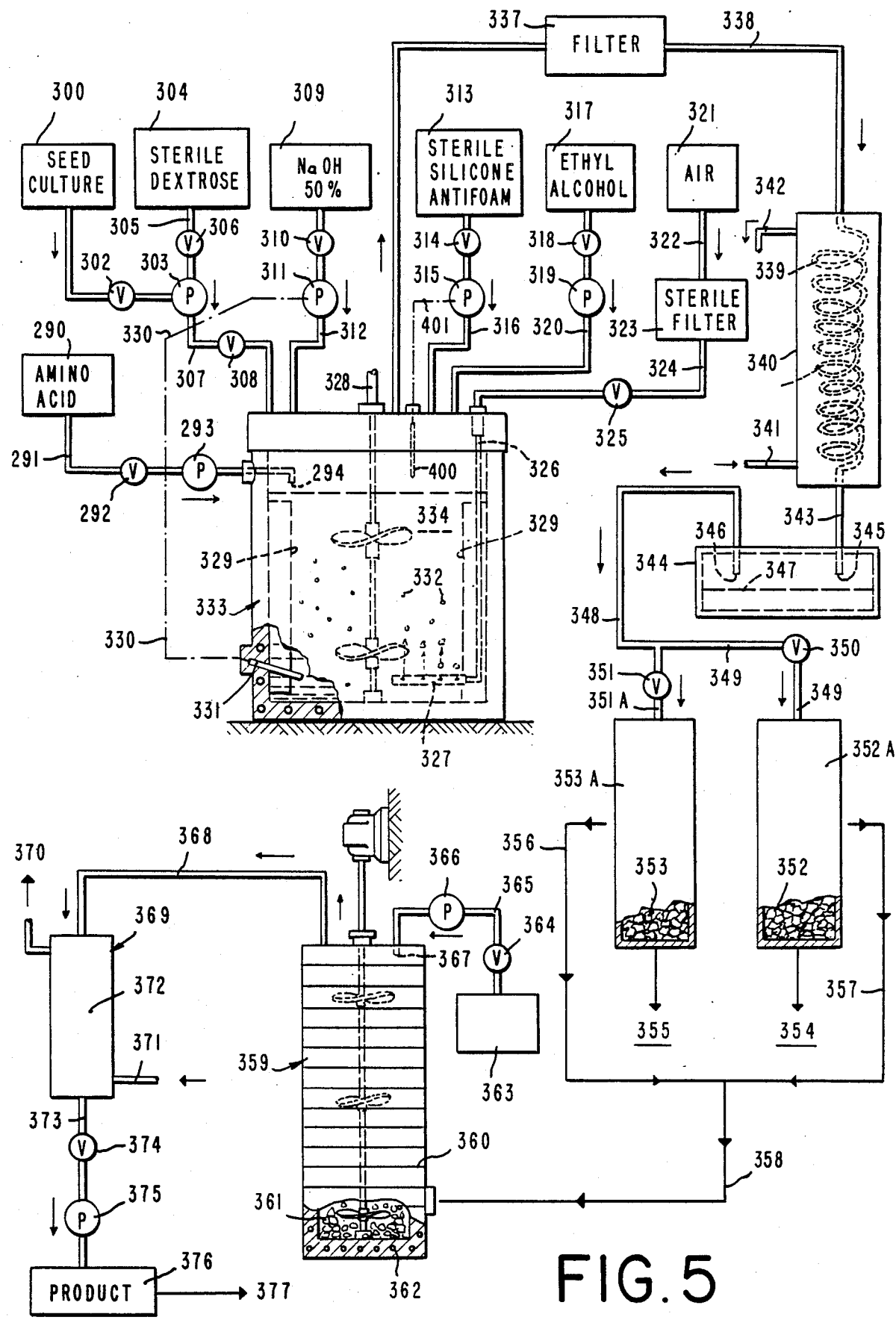

FIG. 5 is a schematic block-flow diagram of a preferred embodiment of the apparatus useful for effecting the process of our invention for preparing esters defined according to the structure:

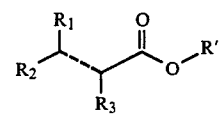

wherein $R_1$, $R_2$ and $R_3$ each represent hydrogen or methyl; wherein the dashed line represents a carbon-carbon single bond or carbon-carbon double bond; wherein R' represents $C_2$-$C_5$ alkyl with the proviso that at least one of $R_1$, $R_2$ and $R_3$ represents methyl.

FIG. 6 is a schematic block-flow diagram of that portion of the apparatus useful in effecting the process of our invention specifically setting forth a configuration of concurrent or parallel charcoal beds useful for adsorbing esters of reaction being evolved from the fermentation vessel of such apparatus.

Figure 7:
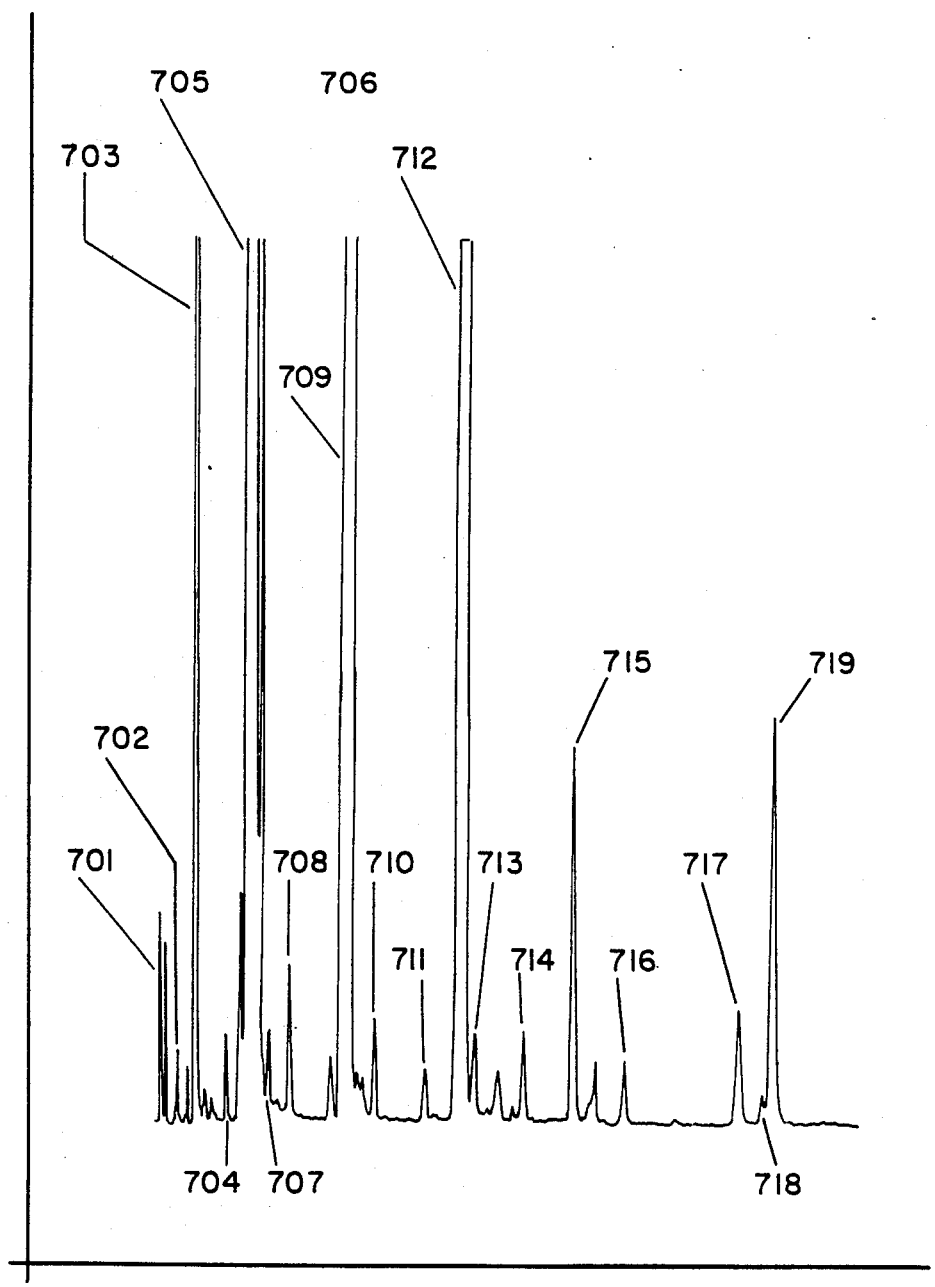

FIG. 7 is the GLC profile for the reaction product of Example I containing various esters produced as a result of the fermentation of isoleucine. (Conditions: 400×0.03 mm SE-30 column programmed at 70°-190° C. at 2° C. per minute).

Figure 8:
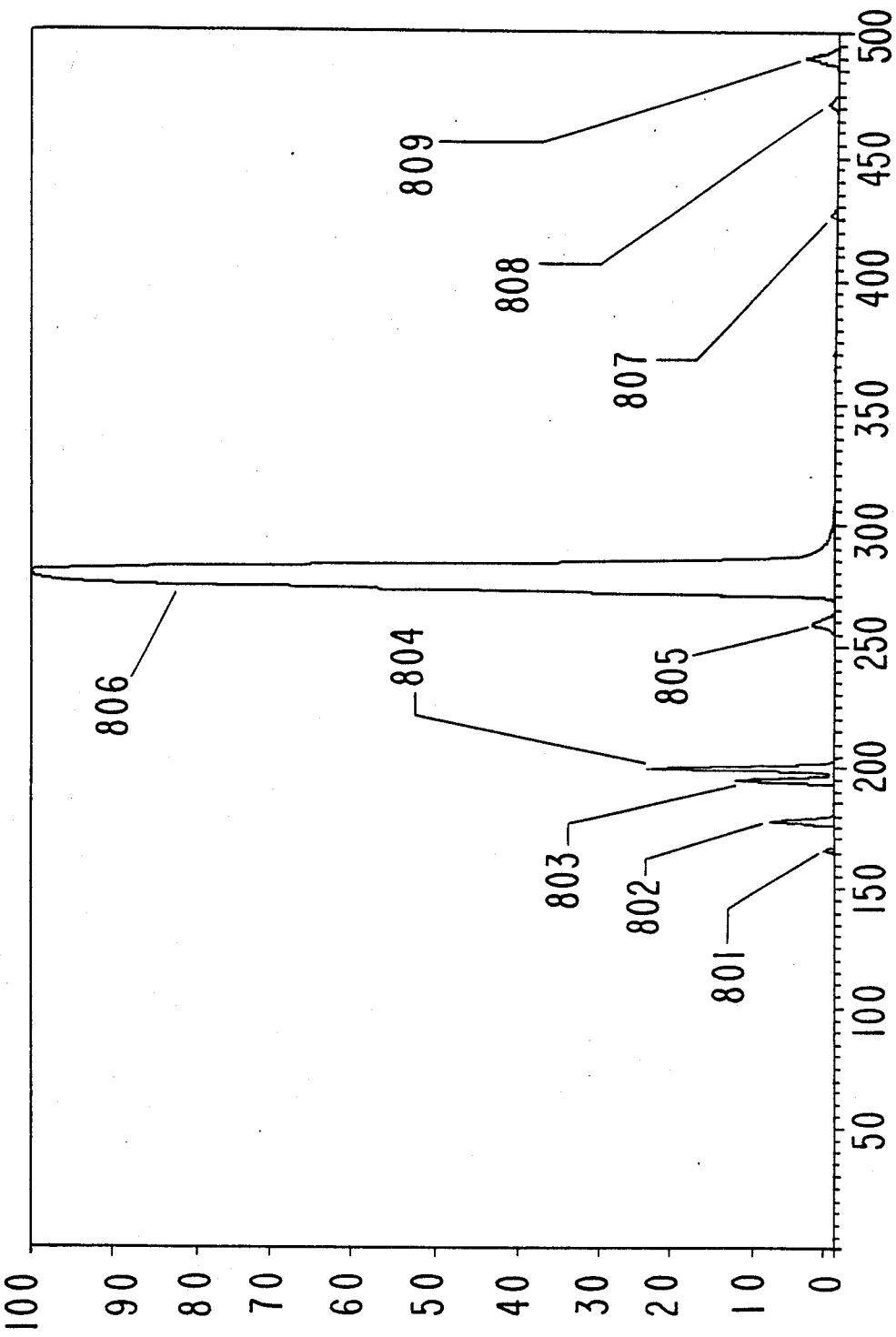

FIG. 8 is the GLC profile for the reaction product of Example II containing esters resulting from the fermentation of leucine.

Figure 9:
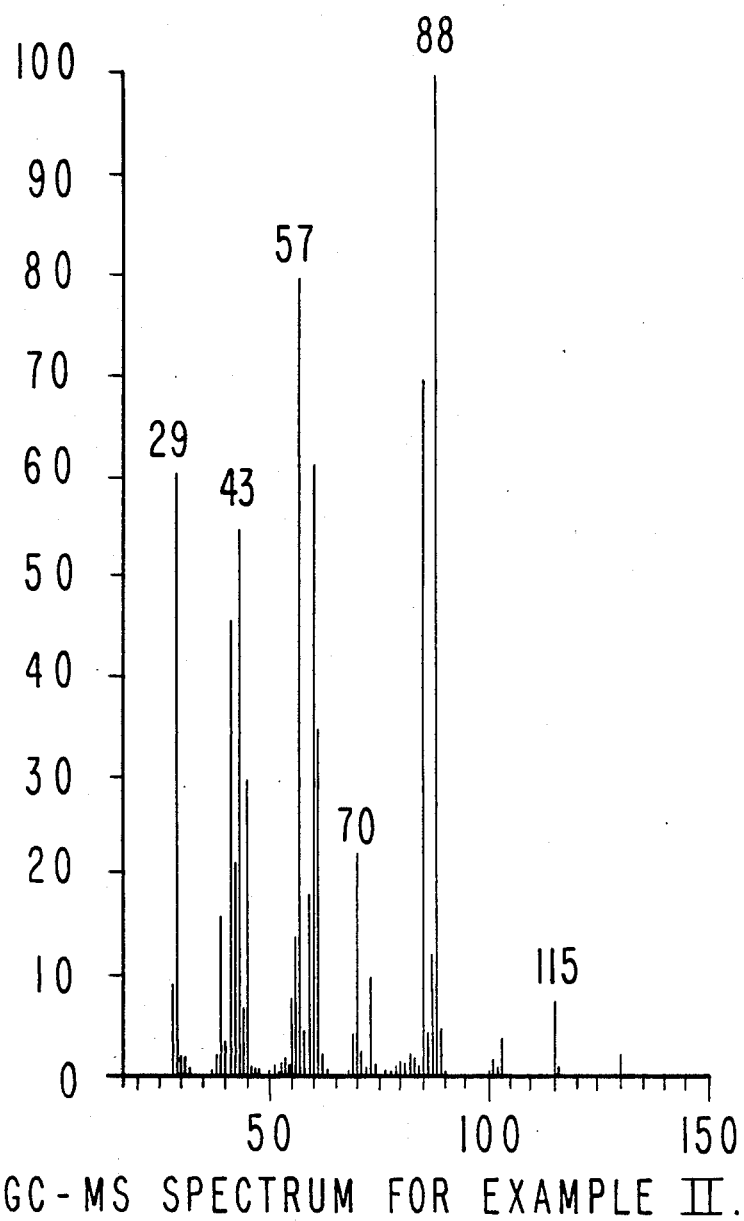

FIG. 9 is the GC-MS spectrum for ethyl isovalerate, the ester of the peak indicated by reference numeral "806" on FIG. 8.

Figure 10:
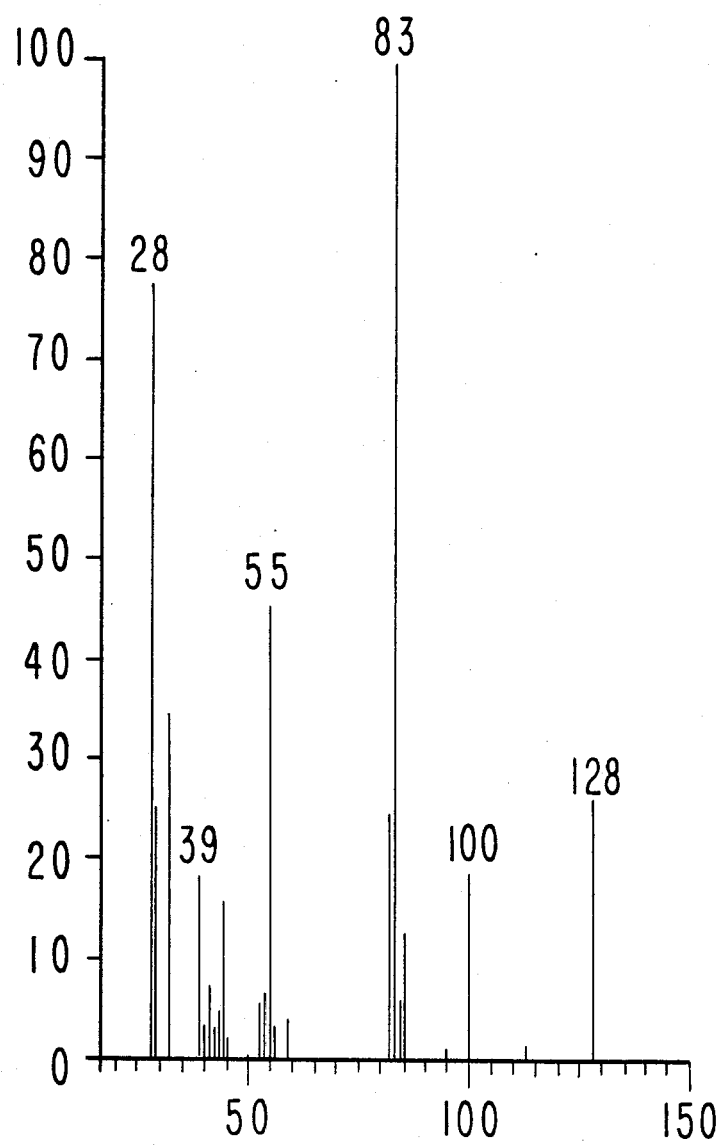

FIG. 10 is the GC-MS spectrum for ethyl senecioate, one of the esters prepared according to Example II and indicated by reference numeral "808" on the FIG. 8 GLC profile.

Figure 11:
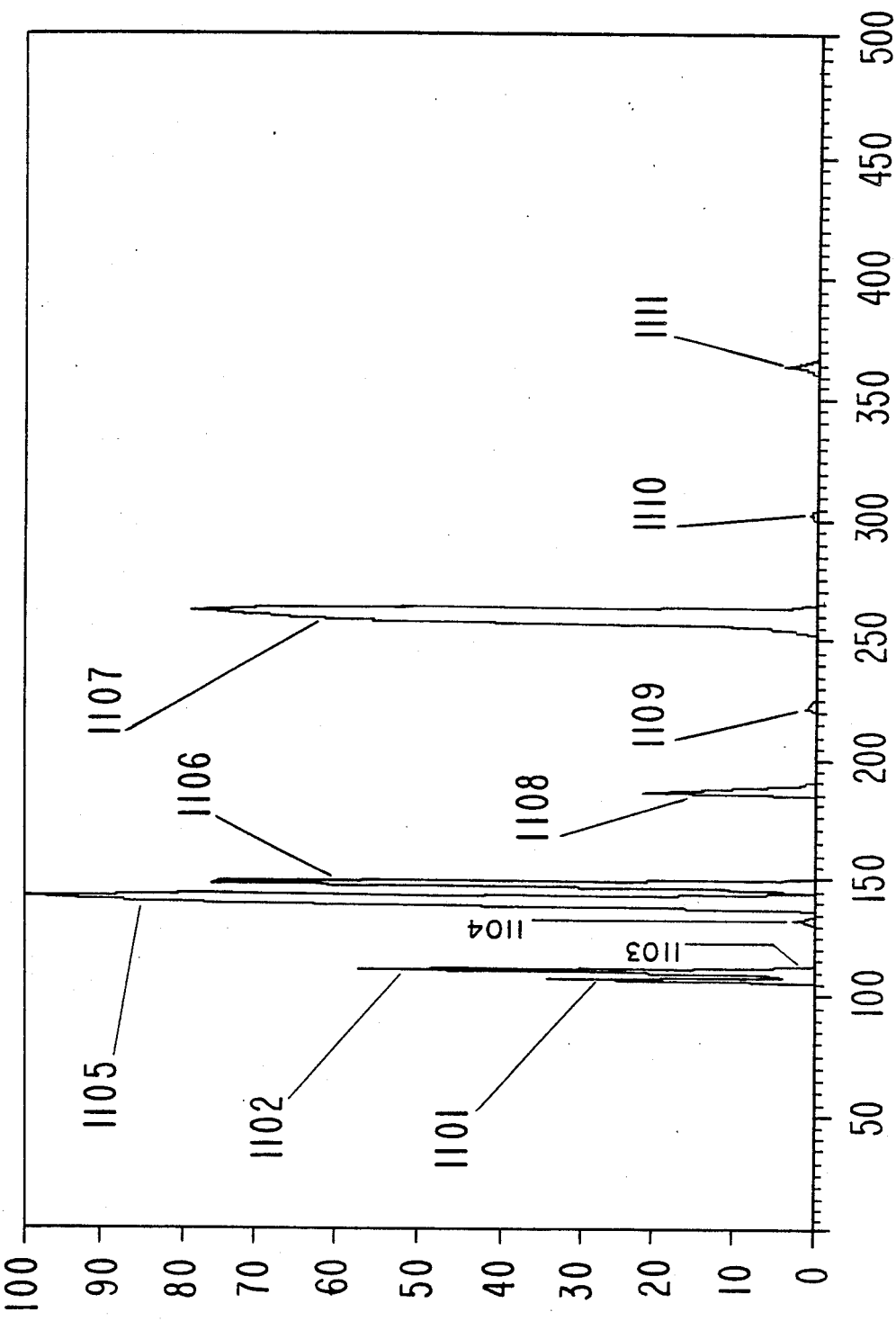

FIG. 11 is the GLC profile for the ester reaction product of Example III containing esters produced as a result of the fermentation of isoleucine in the presence of ethyl alcohol (first charcoal column trap).

FIG. 12 is the GLC profile for the ester-containing reaction product produced as a result of the fermentation of isoleucine of Example III (second charcoal column trap).

FIG. 13 is the GLC profile for the mixture of esters produced according to the reaction involving the fermentation of valine in the presence of ethyl alcohol of Example VIII.

FIG. 14 is the GLC profile of the mixture of esters produced as a result of the fermentation of isoleucine in the presence of isobutanol according to Example IX.

SUMMARY OF THE INVENTION

Our invention relates to a method using fermentation techniques to produce and recover certain naturally-occurring esters found to be useful for their organoleptic properties in augmenting or enhancing the aroma or taste of consumable materials such as foodstuffs, chewing gums, toothpastes, medicinal products, chewing tobaccos, smoking tobaccos, perfume compositions, colognes and perfumed articles, e.g., solid or liquid anionic, cationic, nonionic or zwitterionic detergents, perfumed polymers, fabric softener compositions, fabric softener articles, cosmetic powders, hair preparations and the like which esters are defined according to the structure:

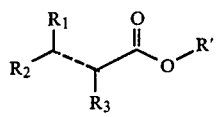

wherein $R_1$, $R_2$ and $R_3$ each represent hydrogen or methyl; $R'$ represents $C_2$–$C_5$ lower alkyl; and the dashed line represents a carbon-carbon single bond or a carbon-carbon double bond with the proviso that at least one of $R_1$, $R_2$ and $R_3$ represents methyl. These esters are produced by means of a fermentation reaction of amino acids defined according to the structure:

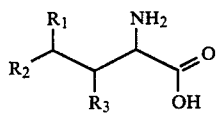

with a $C_2$–$C_5$ lower alkanol according to the reaction:

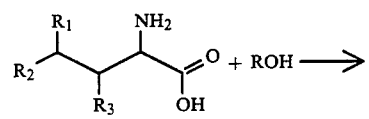

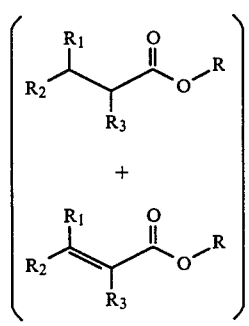

wherein R is the same as $R'$. Of course, the mixtures resulting from the fermentation contain a number of esters in addition to those defined according to the structure:

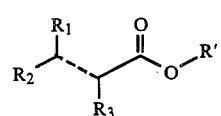

as will become evident from the detailed description of the invention and the examples set forth, infra.

The reaction:

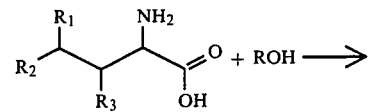

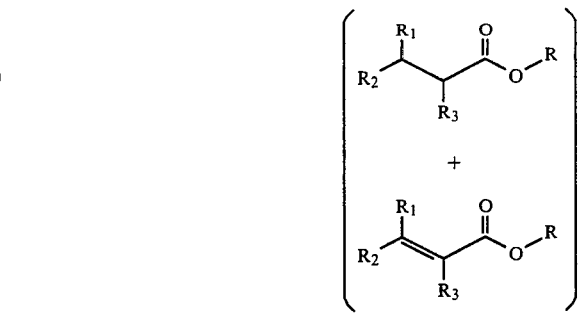

is effected as a result of the presence in the reaction mass of certain organisms, for example:

| | |
|---|---|
| *Brettanomyces anomalus* | ATCC 10559 |
| *Candida krusei* | ATCC 2159 |
| *Ceratocystis moniliformis* | ATCC 12861 |
| *Geotrichum fragrans* (Also known as *Oospora fragrans*) | ATCC 11247 |
| *Geotrichum fragrans* | ATCC 24512 |
| *Geotrichum penicillatum* | CBS 62774 |
| *Geotrichum suaveolens* | CBS 38236 |
| *Hansenula anomala* var. *octosporus* | IAM 4176; 4200 |
| *Hansenula saturnus* (*H. suaveolens*) | ATTC 9847 |
| *Hansenula subpelliculosa* | ATCC 14462 |
| *Kloeckera apiculata* | ATCC 9774; |
| *Kloeckera apiculata* | NRRL Y-1573 (also known as ATCC 10639) |
| *Kloeckera apiculata* | NRRL Y-1380 (also known as ATCC 10634) |
| *Pichia farinosa* | ATCC 2252 |
| *Schizosaccharomyces pombe* | NRRL Y-164 (also known as ATCC 2476) |
| *Schizosaccharomyces pombe* | NRRL Y-9 (also known as ATCC 2478) |
| *Sporobolomyces odorus* (also known as *Sporobolomyces salmonicolor*) | ATTC 26697 |

Note:
CBS stands for Centraalbureau Voor Schimmelcultures, The Netherlands.
IAM stands for Institute of Applied Microbiology, Tokyo, Japan.
AHV stands for the Agriculture Department of Hokkaido University, Sapporo, Japan.

The reaction takes place by bubbling air through the fermenter which contains one or a mixture of the amino acids defined according to the structure:

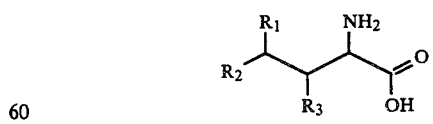

for example, L-leucine, L-isoleucine or L-valine and carbon sources such as:
Dextrose;
Maltose;
Lactose;
Fructose;
Sucrose;

Black strap molasses;
Corn syrup;
Corn syrup solids;
Corn starch; and
Ethyl alcohol.

The concentration range of the amino acid or a mixture of amino acids may vary in the fermenter from about 0.1% by weight of the total contents of the fermenter up to about 1.0% by weight.

The concentration of carbon source in the fermenter based on the weight of total contents of the fermenter is from about 0.5% up to about 8.0%.

Other substrates which may be employed are:
Isobutanol;
Butter Oil; and
Coconut Oil.

The fermentation reaction takes place at a pH of from about 4.0 up to about 7.5 and at a temperature of from about 20° C. up to about 35° C. Preferably, the pH range is 4.75 up to 7.0. Preferably, the temperature range is from about 22° C. up to about 28° C. The time of fermentation may vary from about 20 hours up to about 100 hours, depending upon the other conditions of the fermentation, e.g., temperature of fermentation, rate of aeration, pH of fermentation broth and rate of addition of carbon source. For example, it is preferable to add ethanol to the fermentation broth in order for the ethanol concentration to stay at between 0.8% and 0.9% by weight of the overall fermentation broth.

An important aspect of our invention is in the recovery of the ester reaction product defined according to the structure:

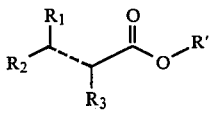

as it is produced in the fermentation process, to wit:

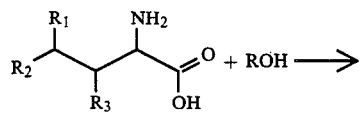

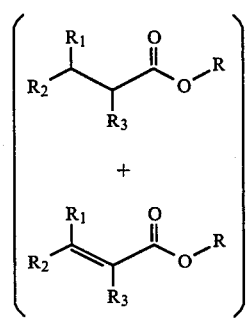

The air that is passed through the fermentation broth during the fermentation, picks up these esters defined according to the structure:

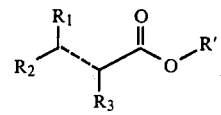

and other useful esters as will become apparent from the detailed description of the invention and the examples, infra. This air stream containing the esters is then passed through a filter; then a condenser and the cooled air containing the esters is then passed through one or more charcoal beds which pick up the esters defined according to the structure:

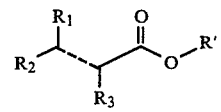

as well as other useful esters. When saturated or when near saturation, the charcoal is removed from the containers holding the charcoal beds and admixed with a suitable liquid distillation material. The mixture of charcoal and the distillation material is placed, separately or simultaneously into a vessel which is then fitted with a distillation column and overhead condenser. Distillation is carried out whereby the esters are recovered from the resulting charcoal/distillation liquid/ester mixture.

The resulting ester mixture can be further refined by means of further fractional distillation and/or by means of preparative GLC.

Among the various useful naturally occurring esters produced according to the process of our invention are:

| ethyl tiglate having the structure: | ethyl-2-methyl butyrate having the structure: |
|---|---|
| ethyl acetate having the structure: | ethyl isobutyrate having the structure: |
| ethyl propionate having the structure: | ethyl isovalerate having the structure: |
| isoamyl isovalerate having the structure: | ethyl senecioate having the structure: |
| isobutyl-2-methyl-butyrate having the structure: and | isobutyl tiglate having the structure: |

DETAILED DESCRIPTION OF THE INVENTION

Figure 1:
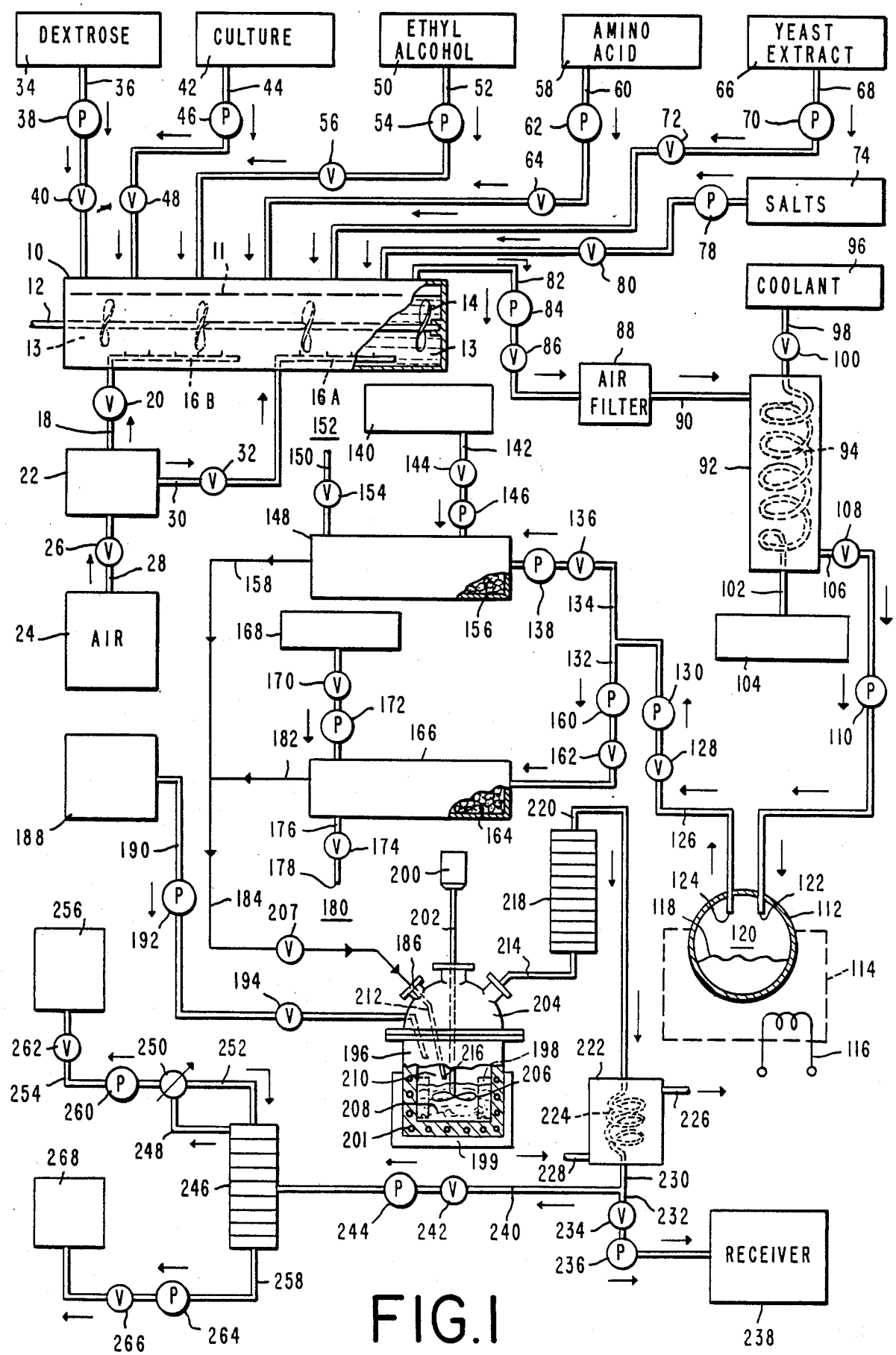
FIG. 1 is a schematic block-flow diagram setting forth apparatus useful in effecting the process of our invention.

In FIG. 1, the reaction:

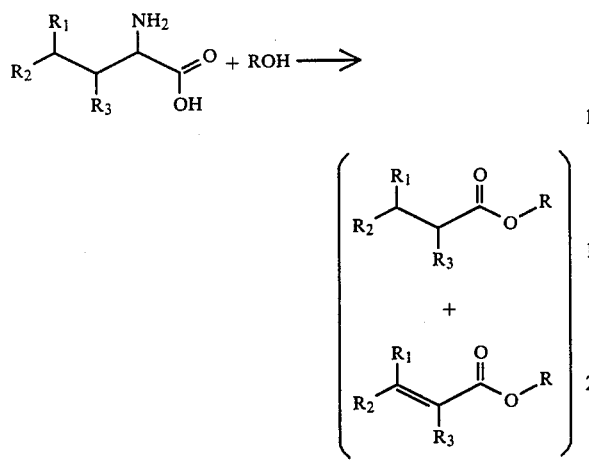

wherein $R_1$, $R_2$ and $R_3$ each represents hydrogen or methyl; and wherein R represents $C_2$–$C_5$ lower alkyl with the proviso that at least one of $R_1$, $R_2$ and $R_3$ is methyl takes place in fermenter 10.

Amino acid having the structure:

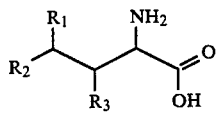

held in tank 58 is fed through line 60 using pump 62 past valve 64 into vessel 10. Ethyl alcohol held in tank 50 is fed through line 52 past valve 56 by means of pump 54 into fermenter 10. Yeast extract in tank 66 is fed through line 68 past valve 72 using pump 70 into fermenter 10.

Dry "salts" or aqueous solutions thereof containing, for example, monobasic potassium phosphate or $MgSO_4.7H_2O$ are fed from tank 74 directly, or through line 76 past valve 80 using pump 78 into fermenter 10.

Inoculum containing culture, for example, a suspension of grown cells of *Geotrichum fragrans* (ATCC 11247) held in Tank 42 is fed through line 44 using pump 46 past valve 48 into fermenter 10.

Carbon source, e.g., dextrose in aqueous solution is fed from holding tank 34 through line 36 past valve 40 using pump 38 into fermenter 10.

The fermenter is stirred using agitator 12 having impellers 14 at a rate of from about 150 rpm up to about 500 rpm. It is preferable to also add to the fermentation batch antifoam prior to the commencement of addition of inoculum from tank 42. Air from vessel 24 is fed through line 28 past valve 26 through filter/manifold 22. Part of the air is distributed through line 30 past valve 32 through sparger 16a into the fermentation batch 13. Part of the air is distributed through line 18 past valve 20 through sparger 16b into the fermentation batch 13 which is held at level 11 in the fermenter 10. Overhead gases are withdrawn from the fermentation batch through line 82 past valve 86 using pump (if desired) 84 past air filter 88 through line 90 past the cooling coils 94 through cooler 92.

The heat exchanger 92 is operated whereby coolant 96 is passed through line 98 past valve 100 through cooling coils 94 into holding tank 104 through line 102. The air coming from heat exchanger 92 containing the esters including those defined according to the generic structure:

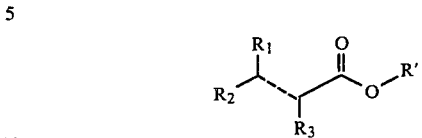

wherein $R_1$, $R_2$ and $R_3$ each represent hydrogen or methyl; wherein the dashed line represents a carbon-carbon single bond or a carbon-carbon double bond; wherein R' represents $C_2$–$C_5$ alkyl with the proviso that at least one of $R_1$, $R_2$ and $R_3$ represents methyl, is passed through line 106 past valve 108 using pump (if desired) 110 to trap 112 where moisture is collected and trapped out of the air in the form of liquid 118. The gas containing the esters emanates at orifice 122 and passes through headspace 120 into orifice 124 through line 126 past valve 128 using pump 130 (if desired) into charcoal bed 156 and/or charcoal bed 164. When being passed only into charcoal bed 156 the ester fermentation product is passed through line 134 past valve 136 using pump 138 (if desired) and valve 162 is in a closed position so that ester cannot be passed through line 132. The ester is adsorbed on the charcoal in charcoal bed 156. In the alternative, when only passing ester into charcoal bed 164, valve 136 is closed and the ester passes through line 132 past valve 162 using pump 160 (if desired). The ester may be passed into charcoal bed 156 until saturation thereof; and then into charcoal bed 164 until saturation thereof. While the ester/air mixture is being passed into charcoal bed 164, charcoal bed 156 may be removed from the container thereof 148 and conveyed via solids conveyor 158/184 into vessel 196. During the adsorption of the esters from the ester/air mixture coming into bed 156 through line 134, non-adsorbed materials and air emanates from the charcoal bed 156 through line 150 past valve 154 into the environment 152.

After all of the ester from the ester/air mixture passed through line 132 is adsorbed onto charcoal bed 164 in holding vessel 166, the vessel 166 is opened and the charcoal having ester adsorbed thereon is conveyed by means of a solid conveyor via lines 182 and 184 into vessel 196.

The non-adsorbed gases and air, during the passage of the ester/air mixture through charcoal bed 164, passes through line 176 past valve 174 into the environment 180 through orifice 178.

When the solid charcoal having ester adsorbed thereon is placed into vessel 196, admixed therewith is distillation liquid aid, e.g., propylene glycol from holding tank 188 through line 190 past valve 194 using pump 192 into vessel 196. In the alternative or simultaneously therewith, distillation liquid aid, e.g., propylene glycol may be pre-mixed with the charcoal bed 156 in vessel 148 by placing in said vessel 148 the distillation fluid aid from holding tank 140 through line 142 past valve 144 using pump 146 into vessel 148. The resulting slurry containing charcoal having adsorbed thereon ester and containing the distillation fluid aid is then pumped via slurry conveyor through lines 158 and 184 past valve 207 through orifice 186 and orifice 216 into vessel 196. In the alternative, the charcoal bed 164 having adsorbed thereon ester is admixed with a distillation fluid aid pre-mixing agent held in tank 168 (e.g., propylene glycol) which is passed through valve 170 using pump 172 into vessel 166. The resulting slurry in vessel 166 containing pre-mixing fluid and charcoal having ester adsorbed thereon 164 is then pumped via slurry conveyor through lines 182 and 184 past valve 207 through orifice 186 and orifice 216 into vessel 196.

The resulting slurry 208 held in tank 196 is then distilled while being stirred using stirrer 202 driven by stirring motor 200 fitted with impeller 206 and, optionally, using baffles 198. The vessel 196 and contents thereof are heated using heated coil 201 and heater 199. The vessel 196 is fitted with a head 204 which is fitted with a distillation column 218 as well as the agitator 208 and (not shown) a temperature control device.

The distillation proceeds whereby the ester passes through headspace 210 through line 214 into batch distillation column 218 through line 220 through cooling heat exchanger 222 through coils 224 (part of the heat exchanger) and then through line 230 where the resulting material may be placed in receiver 238 through line 232 past valve (open) 234 using pump 236 (with valve 242 of line 240 being closed). The heat exchanger 222 is cooled by means of coolant passing into the heat exchanger at 228 and out at 226 (via a countercurrent heat exchange unit operation). In the alternative, valve 234 may be closed and the resulting ester mixture may be passed through line 240 past valve 242 (open) using pump 244 into fractionation column 246. The resulting ester mixture may then be fractionated whereby the overhead lighter boiling esters (e.g., ethyl propionate) are passed through line 248 and refluxed using reflux cutter 250 with the refluxing portion being passed back into the distillation column at the top plate via line 252 and the remainder of the overhead light boilers being passed through line 254 using pump 260 past valve 262 into holding tank 256. By the same token, the bottoms from the distillation column 246 are passed through line 258 past valve 266 using pump 264 into holding vessel 268.

Figure 2:
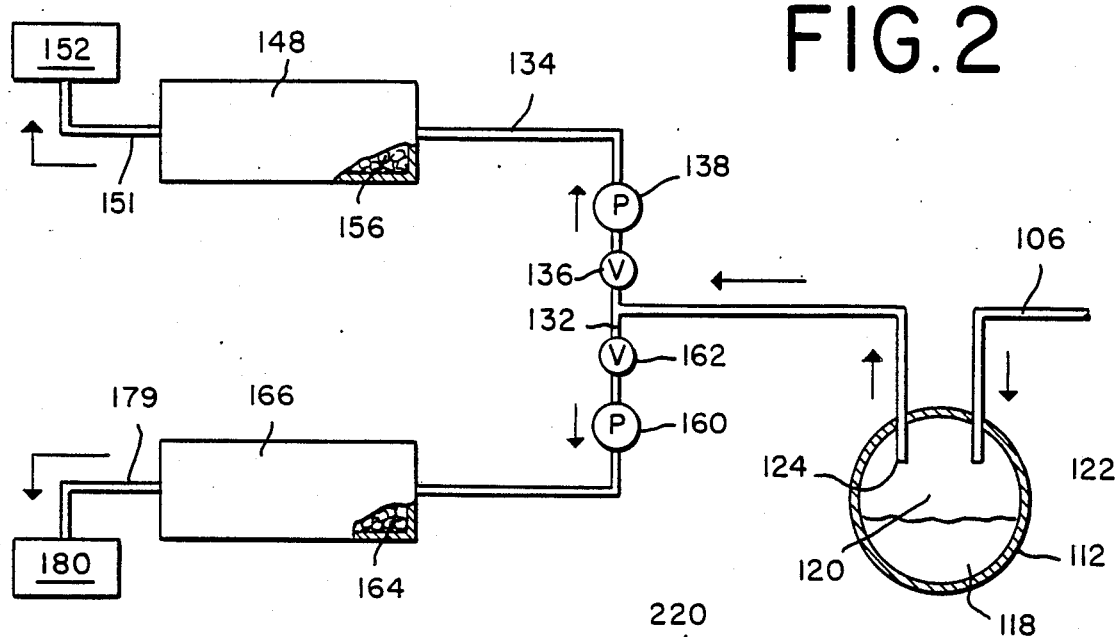
FIG. 2 is a blown up block-flow schematic diagram of that portion of apparatus useful in effecting the process of our invention where the esters defined according to the structure.

FIG. 2 is a section of the apparatus of FIG. 1 in detail showing the condensate trap 112 and the charcoal bed vessels 148 and 166 holding charcoal beds 156 and 164 (without the optional fluid pre-mix agent feeding means for each of the charcoal beds).

FIG. 3 is a section of the apparatus of FIG. 1 in detail showing the loading of ester-adsorbed charcoal solids 156 or 164 or a combination thereof into hopper 187 through feeding line 189 connected at orifice 186 through line 191 through orifice 216 into the distillation vessel. The slurry 208 is made up by admixing the charcoal bed material 156 and/or 164 with distillation aid fluid from tank 188 which is pumped through line 190 using pump 192, past valve 194 into the slurry 208. Distillation column 218a is fitted onto head 204a ready for distillation.

After removal of the hopper 187 which was used for ester-adsorbed charcoal loading (for loading 156 and/or 164,), the hopper is removed and replaced by line 286 at orifice 186 which has a valve 209 located in said line. The valve is closed and the stirring motor 200 is engaged whereby impeller 206 causes the slurry 208 to become agitated. The distillation takes place through distillation column 218b as shown in FIG. 4. At the time of the distillation valve 194 and valve 209 are in "closed" position with stirring motor 200 in operation.

FIG. 5 sets forth a preferred apparatus configuration for the carrying out of the process of our invention.

Fermentation vessel 333 is equipped with baffles 329 and stirrer 328.

All additions to fermenter 333 are made through sterile lines.

Sterile dextrose (50% aqueous solution) from holding tank 304 and seed culture from tank 300 are pumped using pump 303 through line 305 past valve 306 (for the sterile dextrose) and through line 301 past valve 302 (for the seed culture) jointly through line 307 past valve 308 into the fermentation vessel 333. 75 Percent aqueous ethyl alcohol is pumped from holding tank 317 through valve 318 using pump 319 through line 320 into fermenter 333.

From holding tank 290, amino acid defined according to the generic structure:

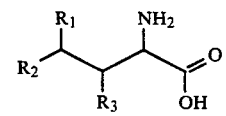

(either individually or in admixture) with yeast extract, salts, and emulsifier (e.g., TWEEN ®80) are pumped through line 291 past valve 292 using pump 293 through orifice 294 into the fermentation batch 334. Air is fed from vessel 321 through line 322 through sterile filter 323 through line 324 past valve 325 through sparger 326 and 327 into the fermentation batch 334 (air bubbles indicated by reference numeral "332"). During the fermentation, sodium hydroxide (50% aqueous solution, for example) is fed from holding tank 309 past valve 310 using pH probe (331) controlled pump 311 into the fermentation vessel 333 and antifoam (e.g., silicone antifoam) is pumped from holding tank 313 through valve 314 and line 316 using controlled pump 315 controlled via control line 401 and foam probe 400. During the fermentation the esters formed primarily including those having the formula:

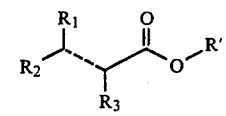

wherein $R_1$, $R_2$ and $R_3$ each represent hydrogen or methyl; wherein the dashed line represents a carbon-carbon double bond or a carbon-carbon single bond; wherein $R'$ is $C_2-C_5$ alkyl with the proviso that at least one of $R_1$, $R_2$ and $R_3$ represents methyl, is "distilled" from the fermentation mass 334 by mass transfer of the said esters into the air bubbles 332. The ester/air gas mixture passes through line 336 through filter 337 and line 338 through heat exchanger 340 (through coils 339). The heat exchanger is cooled, for example, in a countercurrent fashion by coolant entering at 341 and leaving at 342. The cooled ester-air gas mixture passes through line 343 into condensate trap 344 (from orifice 345) where condensate is collected at 347. The ester-air gas is then passed through line 348 (entry point at 346) into either charcoal bed 353 (held in vessel 353A) or charcoal bed 352 (held in vessel bed 352A). When the ester-air gas is passed through charcoal bed 352 alone, valve 351 is closed preventing the ester-air gas mixture from being conveyed through line 351A. Instead, the ester-air mixture is conveyed through line 349 passed valve 350 into charcoal bed 352. The non-adsorbed gases exit after the ester is adsorbed on the charcoal, at 354.

When charcoal bed 353 is in use (held in vessel 353A) then valve 351 is open and valve 350 is closed. Thus, the ester-air mixture passes through line 351A through valve 351 into charcoal bed 353. The non-adsorbed gases and air exits at 355.

When the charcoal beds are saturated, the charcoal is removed from the vessels (e.g., vessel 353A and conveyed via 356 (e.g., a solid conveying line) through line 358 into distillation apparatus 359. In the alternative, the charcoal having adsorbed thereon ester 352 is removed from vessel 352A via solid conveyance means 357 through line 358 into vessel 359. Also added to the distillation vessel 359 is distillation fluid aid (e.g., propylene glycol) from holding tank 363 through line 364 using pump 366 (if desired) through orifice 367 into the distillation vessel 359. The distillation vessel in operation is heated using heating coil 362. The ester distillate is passed through line 368 through condenser 369. The condenser is cooled, for example, (in a countercurrent fashion) by adding cooling fluid at 371 and exiting the cooling fluid at 370. The condenser (indicated by reference numerals "369" and "372") is connected to exit line 373. The condensed esters are passed through line 372 past valve 374 (open) using pump 375 into product containment means 376 and then sent on for further purification or fractionation via line 377.

The sterile dextrose carbon source may be added, preferably, all at once immediately prior to inoculation of the seed culture from 300.

The seed culture from holding tank 300 can be pumped into the fermenter, preferably, through the same pump and lines used for the dextrose addition from tank 304, that is, pump 303 and the preferable configuration is that which is shown in FIG. 5.

Neither the ethanol nor pH controlling sodium hydroxide solutions need be sterilized since they are inherently sterile. Nevertheless, the orifice entry points of the sodium hydroxide and the ethanol should be sterile.

FIG. 6 is a detailed schematic diagram of that section of the apparatus of FIG. 5 setting forth the configuration of the charcoal beds 352 and 353.

Thus, through line 348 the ester-air mixture is passed either simultaneously into both charcoal beds 352 and 353 through line 349 past valve 350 and line 351A past valve 351, respectively. When such is the case, valve 457 of line 456 and valve 459 of line 458 and the air (without adsorbed ester) passes through lines 354 and 355 past valves 452 and 454 through lines 453 and 455 into the atmosphere at 462 and 463 (valve 451 being closed). In the alternative, the charcoal beds 353 and 352 can be operated in series where the ester-air mixture first passes through charcoal bed 352 and then passes through charcoal bed 353 thereby causing the adsorption and entire process to be more efficient. Thus, for example, valve 351 is in a closed position and valve 350 is in an open position. Valve 459 is closed and valve 457 is open. Valves 454 and 452 are closed and valve 451 is open. In this manner, the ester-air gas mixture passes through line 348 through line 349 past valve 350 into charcoal bed 352 where 70% of the ester, in the ester-air mixture is adsorbed. The remaining ester-air mixture is passed through lines 354 and 450 past valve 451 through line 355 into charcoal bed 353 where the remaining ester of the ester-air mixture is adsorbed. The air and unadsorbed gases then passes through line 456 past valve 457 into the atmosphere at 461.

Thereafter, the charcoal beds having ester adsorbed thereon, 352 and 353 are removed at 356 and 357 for subsequent slurification and distillation as indicated in FIG. 5.

In the alternative, the configuration of FIG. 6 is even more flexible, in that, charcoal beds 352 and 353 can be operated sequentially as the case with the charcoal beds of FIG. 2. In the first instance, valves 351 and 459 are closed as is valve 451. The ester-air mixture passes through line 348 and line 349 past valve 350 into bed 35. The remaining gases, mostly unadsorbable gases, and air pass through 354 past valve 452 through line 453 to the atmosphere 462. At saturation (that is, when the charcoal bed is saturated with adsorbed ester) valve 350 is closed, valve 451 remains closed, valve 457 is closed and valve 351 is open. The ester-air mixture passes through line 348, line 351A into charcoal bed 353. The unadsorbable gases and air pass through line 355 through valve 454 through line 455 to the atmosphere at 463.

The following examples are descriptive runs employing the process in accordance with our discovery. Particular amounts of materials or particular types of feedstocks employed, particular species or strains of organisms including yeast should be considered as illustrative and not as limitative of our invention.

EXAMPLE I

In apparatus of FIG. 1, into fermenter 10 is placed 1 liter of an inoculum of Geotrichum fragrans (ATCC 11247); enough isoleucine to make up a 0.3% solution; 6% aqueous dextrose 0.05% $MgSO_4.7H_2O$ and 0.02% TWEEN ®80 (polyoxyethylene[20]sorbitan mono-oleate).

The agitation rate in the fermenter is 400 rpm and the temperature is set at 25° C. The aeration rate is 16 liters per minute. The pH is maintained in the range of 5.05 up to 5.25.

The reaction taking place is basically as follows:

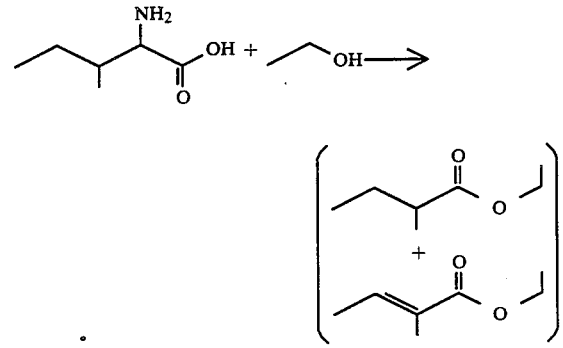

Ethanol is added to the reaction mass at a rate of 10 ml per hour (total amount of ethanol 250 ml over a period of 25 hours).

The total amount of adsorbent charcoal in charcoal bed 156 is 250 grams.

The ester-adsorbed charcoal was treated with steam and ester-containing condensate is collected. 10 Grams of this ester-containing condensate are admixed with 10 ml of distilled water and then extracted three times with 15 ml of FREON ®11. The combined Freon extracts are dried over anhydrous magnesium sulfate and concentrated by nitrogen stream to 0.5 grams. The resulting concentrated extract is analyzed by GCMS and the results are as follows:

TABLE I

| Peak No. | Component Identified | % of Extract | % of Total Sample |
|---|---|---|---|
| 701 | FREON ® 11* | | |
| 702 | Ethyl acetate | 0.02 | 0.001 |
| 703 | Isobutanol | 4.28 | 0.214 |
| 704 | Ethyl propionate | 0.05 | 0.0025 |
| 705 | Isoamyl alcohol | 49.18 | 2.459 |
| 706 | Ethyl isobutyrate | 1.12 | 0.056 |
| 707 | Isobutyl acetate | 0.09 | 0.0045 |
| 708 | Ethyl butyrate | 0.14 | 0.007 |
| 709 | Ethyl-2-methyl butyrate | 28.61 | 1.4305 |
| 710 | Isoamyl acetate | 0.13 | 0.0065 |
| 711 | Isobutyl isobutyrate | 0.06 | 0.003 |
| 712 | Ethyl tiglate | 13.71 | 0.6855 |
| 713 | Propyl-2-methyl butyrate | 0.10 | 0.005 |
| 714 | 1-Ethoxy-1-butoxy-2-methyl ethane | 0.11 | 0.0055 |
| 715 | Isobutyl isovalerate | 0.49 | 0.0245 |
| 716 | Propyl tiglate | 0.08 | 0.004 |
| 717 | Isobutyl tiglate | 0.16 | 0.008 |
| 718 | Isoamyl isovalerate | 0.04 | 0.002 |
| 719 | Amyl isovalerate | 0.64 | 0.032 |
| | | 99.01% | 4.9505 |

*Solvent used for extraction.

FIG. 7 is the GLC profile of the above mixture (conditions: 400 mm × 0.03 mm glass capillary column (SE-30) programmed at 70°–190° C. at 2° C. per minute). The peaks indicated as set forth above are also indicated on the GLC profile and these peaks stand for the components identified in the foregoing Table I.

The resulting product has a fruity, apple, strawberry-like, minty aroma and taste profile at 3 ppm causing it to be useful in apple, pear and strawberry fruit flavors.

At the rate of 4 ppm, the resulting product was added to SUNKIST ® orange beverage syrup and a beverage was produced. The resulting product has an excellent natural orange aroma and taste profile with apple, pear and strawberry undertones.

The foregoing example is repeated with conditions set forth in Table II, infra yielding a percentage of the "main two esters" namely, ethyl tiglate and ethyl-2-methyl butyrate:

EXAMPLE II
PREPARATION OF ESTER MIXTURE

Reaction:

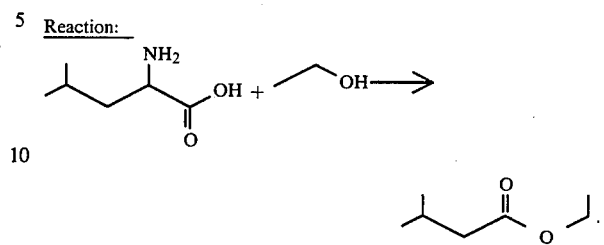

Over a period of three days, 1 liter of inoculum suspension of Geotrichum fragrans (ATCC 11247) is grown. The inoculum is added to the fermenter 333 from holding tank 300 in FIG. 5.

Leucine having the structure:

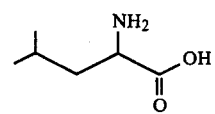

is added to the fermentation batch (in order to bring the entire percentage to 0.55% leucine), the working volume of the fermentation batch being 22 liters. From holding vessel 304 sterile CERELOSE ® in aqueous solution (50%) is added to fermentation vessel 333 in order to create a percentage of CERELOSE ® in the fermentation vessel of 6%. Also added to the fermentation vessel 333 AMBEREX ® to create a percentage of 0.1% AMBEREX ®; $MgSO_4.7H_2O$ in order to bring its level to 0.05%; $KH_2PO_4$ in order to bring its level to 0.1% and TWEEN ®80 in order to bring its level to 0.02%.

The fermenter is agitated at a speed of 400 rpm. Aeration is commenced at a rate of 16 liters per minute. Charcoal traps 352 and 353 are set up containing, respectively, 300 grams and 150 grams of charcoal. The pH is maintained with sodium hydroxide from holding vessel 309 at a level of between 5.05 and 5.25. Into holding vessel 363 is placed propylene glycol which will be used to slurry with ester-adsorbed charcoal from charcoal beds 352 and 353.

Over a period of 24 hours, ethyl alcohol is added to the reaction mass whereby the percentage of ethyl alcohol in the reaction mass is maintained at between 0.65% and 0.675%. The total amount of ethyl alcohol added to the reaction mass is 500 ml (75% ethanol solution added

TABLE II

| RUN | % Isoleucine | % Sucrose | % TWEEN ® 80 (Emulsifier) | % Ethyl Alcohol | % Inoculum | Aeration L/P/L/P Min. of Air | RPM (Agitation) | Temperature (°C.) | pH | Product: Grams Per Liter of Main Two Esters |
|---|---|---|---|---|---|---|---|---|---|---|
| I-1 | 0.5 | 5 | 0 | 0 | 4.5 | 0.5 | 300 | 24–26 | 5.00–5.10 | 2.6 |
| I-2 | 0.5 | 5 | 0 | 0 | 4.5 | 0.5 | 300 | 25–32 | 5.00–5.10 | 2.15 |
| I-3 | 1.0 | 10 | 0 | 0.53–0.82 | 4.5 | 0.5 | 300 | 24–26 | 5.05–5.10 | 2.5 |
| I-4 | 1.0 | 5 | 0 | 0 | 4.5 | 1.0 | 300 | 24–26 | 6.5 | 1.3 |
| I-5 | 1.0 | 5 | 0 | 0.65–1.32 | 4.5 | 0.5 | 300 | 24–26 | 5.05–0.05 | 2.25 |
| I-6 | 0.5 | 6 | 0 | 0.2–0.6 | 4.5 | 0.5 | 300 | 24–26 | 5.00–5.10 | 2.02 |
| I-7 | 0.55 | 6 | 0.02 | 0.02–0.61 | 4.5 | 0.5 | 300 | 24–26 | 5.00–5.10 | 2.74 |
| I-8 | 0.55 | 6 | 0.02 | 0.19–0.68 | 4.5 | 0.73 | 400 | 24–26 | 5.00–5.10 | 2.01 |
| I-9 | 0.55 | 6 | 0.02 | 0.17–0.56 | 4.5 | 0.73 | 400 | 24–26 | 5.00–5.10 | 2.26 |
| I-10 | 0.55 | 6 | 0.02 | 0.49–0.82 | 4.5 | 0.73 | 400 | 24–26 | 5.00–5.10 | 3.0 |
| I-11 | 0.55 | 6 | 0.02 | 0.48–0.84 | 1.0 | 0.73 | 400 | 24–26 | 5.00–5.10 | 3.16 |
| I-12 | 0.4 | 4.5 | 0.02 | 0.6–0.8 | 4.5 | 0.73 | 400 | 26–26 | 5.00–5.10 | 3.16 | to fermenter 333 from holding vessel 317 through line 320).

The ester-adsorbed charcoal is admixed with the propylene glycol in batch distillation apparatus 359 and the distillation takes place using condenser 372. The ester mixture collected in the product (together with other materials) is analyzed and the GLC profile is set forth in FIG. 8 (conditions: Chromosorb 101, 6'×0.125" column programmed at 100°–250° C. at 20° C. per minute).

The peak indicated by reference numeral "801" is the peak for ethyl acetate. The peak indicated by reference numeral "802" is the peak for ethanol (unreacted). The peak indicated by reference numeral "803" is the peak for ethyl propionate. The peak indicated by reference numeral "804" is the peak for ethyl isobutyrate. The peak indicated by reference numeral "805" is the peak for ethyl-2-methyl butyrate. The peak indicated by reference numeral "806" is the peak for ethyl isovalerate. The peak indicated by reference numeral "807" is the peak for isoamyl alcohol. The peak indicated by reference numeral "808" is the peak for ethyl senecioate. The peak indicated by reference numeral "809" is the peak for ethyl tiglate. The majority of the material produced is, however, ethyl isovalerate. The ethyl isovalerate has the structure:

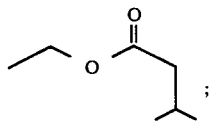

ethyl senecioate has the structure:

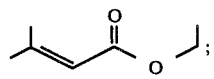

and ethyl tiglate has the structure:

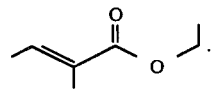

FIG. 9 is the GCMS spectrum for ethyl isovalerate.
FIG. 10 is the GCMS spectrum for ethyl senecioate.

EXAMPLE III

PRODUCTION OF ESTER MIX

Reaction:

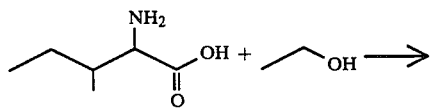

-continued
Reaction:

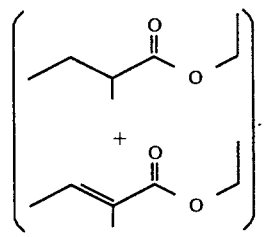

An inoculum is produced in an 1 liter batch over a period of 24 hours by growing *Geotrichum fragrans* (ATCC 11247).

Using the fermenter of FIG. 5 (fermenter 333), an example similar to that is carried out except instead of leucine, isoleucine having the structure:

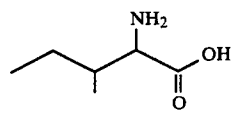

is used as a precursor.

The temperature of the fermentation is 25° C. The agitation rate is 400 rpm. The aeration rate is 0.73 liter per minute per liter. The pH range is maintained at the range of from 5.05 up to 5.35. The sugar used is CERELOSE ®2001 at a level of 6% in the fermentation batch (using a 50% solution sterilized separately). The isoleucine level in the fermenter is 0.55% at the beginning. The amount of $KH_2PO_4$ in the fermenter initially is 0.1%. The amount of $MgSO_4.7H_2O$ is 0.05%. The amount of TWEEN ®80 initially in the fermenter is 0.02%. The amount of silicone antifoam is added periodically to prevent foaming from holding vessel 313 through line 316 into fermenter 333 and the addition of the silicone antifoam is controlled using foam probe 400. Over a period of 48 hours, 450 ml of 75% ethyl alcohol is added to fermenter 333 in FIG. 5 from holding vessel 317 at the rate of 11 ml per hour whereby the percent of ethanol in the fermentation batch 334 is between 0.49% and 0.82%.

The esters produced from the fermentation are trapped in charcoal bed 352 held in vessel 352A and in charcoal bed 353 held in vessel 353A. The amount of charcoal in vessel 352 is 300 grams (yielding 71.5 grams ester). The amount of charcoal in trap 353 is 150 grams (containing 11.7 grams of mixture of ester).

The ester-adsorbed charcoal batches are placed in distillation vessel 359 at 361 and admixed with propylene glycol (250 ml). The resulting slurry is distilled through distillation column 359 using plates 360 through line 368 and condenser 369/372 through line 374 into a product holding tank 376.

FIG. 11 is the GLC profile for the ester mixture thus collected. (Conditions: 50 meter at 0.32 mm fused silica (carbowax 20M column programmed at 75°–225° C. at 2° C. per minute).

The peak indicated by reference numeral "1101" is the peak for ethyl propionate. The peak indicated by reference numeral "1102" is the peak for ethyl isobutyrate. The peak indicated by reference numeral "1103" is the peak for the silicone defoamer. The peak indicated by reference numeral "1104" is the peak for ethyl butyrate. The peak indicated by reference numeral "1105" is the peak for ethyl-2-methyl butyrate. The peak indicated by reference numeral "1106" is the peak for ethyl isovalerate. The peak indicated by reference numeral "1107" is the peak for ethyl tiglate. The peak indicated by reference numeral "1108" is the peak also for silicone antifoam. The peak indicated by reference numeral "1109" is the peak for 2-methyl-1-butanol. The peak indicated by reference number "1110" is the peak for isoamyl isovalerate. The peak indicated by reference numeral "1111" is also a peak for the silicone defoamer.

FIG. 11 is the GLC profile for the first ester trap, that is, the ester found in charcoal batch 352.

FIG. 12 is the GLC profile for the ester adsorbed on the second charcoal trap, that is, trap 353. (Same conditions as for GLC profile of FIG. 11).

The peak indicated by reference numeral "1201" is the peak for ethyl acetate. The peak indicated by reference numeral "1202" is the peak for ethanol. The peak indicated by reference numeral "1203" is the peak for ethyl propionate. The peak indicated by reference numeral "1204" is the peak for ethyl isobutyrate. The peaks indicated by reference numeral "1205" are peaks for propionaldehyde propylene glycol acetal. The peak indicated by reference numeral "1206" is the peak for ethyl isovalerate. The peak indicated by reference numeral "1205A" is the peak for ethyl-2-methyl butyrate. The peak indicated by reference numeral "1207" is for the silicone defoamer. The peak indicated by reference numeral "1208" is the peak for 2-methyl-1-butanol. The peak indicated by reference numeral "1209" is the peak for ethyl tiglate. The peak indicated by reference numeral "1210" is the peak for isoamyl isovalerate and n-amyl isovalerate. The peak indicated by reference numeral "1211" is the peak for the silicone defoamer.

EXAMPLE IV

PREPARATION OF ESTER MIX

Reaction:

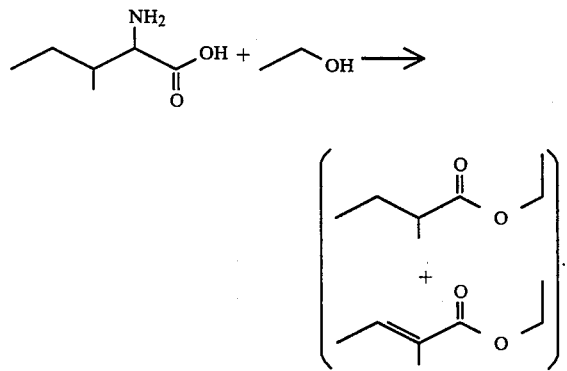

Over a three day period 90 ml of an inoculum of *Geotrichum fragrans* (ATCC 24512) is grown.

Utilizing the apparatus of FIG. 5 and the procedure of Example II, into fermenter 333 is added dextrose in order to achieve a level of 5% dextrose in the fermentation batch (total volume: 3.5 liters). 4 ml Antifoam is added and 40 ml ethanol is added. The aeration is carried out at a level of 2 liters per minute. The fermentation batch is stirred at 400 rpm and the pH is maintained at a level of 6.5–6.7 using 1 molar potassium hydroxide solution.

Two resin (polyvinyl benzenesulfonic acid resin) columns 352 and 353 each contain 100 grams of AMBERLITE ®XAD-2 resin.

23 gm Isoleucine is added to the fermentation batch.

The fermentation reaction proceeds for a period of three days. The resin beds are then extracted with FREON ®113 and the freon extracts are washed with 30% sodium bicarbonate and sodium chloride and then dried over anhydrous sodium sulfate. The solvent is evaporated under nitrogen yielding 2.04 grams of residue. The residue is distilled at atmospheric pressure yielding two fractions: the first fraction contains 62.1% ethyl-2-methyl butyrate and 19.13% ethyl tiglate and the second fraction contains 28.5% ethyl-2-methyl butyrate and 27.4% ethyl tiglate.

EXAMPLE V

PREPARATION OF ESTER MIXTURE

Reaction:

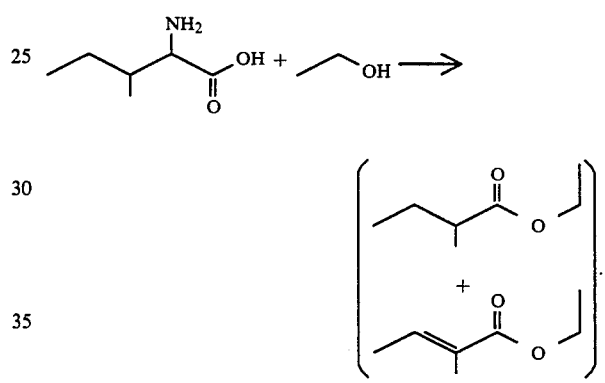

Over a period of 49 hours, 100 ml of inoculum of *Geotrichum fragrans* (ATCC 11247) is grown.

Using the apparatus of FIG. 5 and the procedure of Example II, 3 liters of a fermentation batch is made up containing 5% dextrose and 0.55% isoleucine.

The fermentation is run at 25° C.; the stirring rate is 400 rpm and the air rate is 4 liters per minute. The pH is controlled and kept at 6.5 using 1 molar potassium hydroxide.

Ethanol is added over a period of 72 hours in the amount of 40 ml. At the end of 120 hours, the fermenter is stopped and the 100 gram charcoal traps (jacketed at 10° C. throughout the procedure) are stripped with steam until a total of 1000 ml of steam distillate is collected. The steam distillate is extracted with FREON ®113 and the extract is dried over anhydrous sodium sulfate. The solvent is removed yielding a total ester content of 1.42 grams containing 81.55% ethyl-2-methyl butyrate and 4.6% ethyl tiglate.

The contents of the fermenter is transferred to a 5 liter flask and distilled at 32° C. and 35 mm/Hg pressure to yield 200 ml of liquid. The resulting distillate is extracted with FREON 113 yielding 45 mg of ester mixture.

The charcoal traps are then extracted with acetone and the acetone is dried. The solvent is removed yielding 5.38 grams of ester containing 23% ethyl-2-methyl butyrate and 13.7% ethyl tiglate.

EXAMPLE VI

PREPARATION OF ESTER MIXTURE

Reaction:

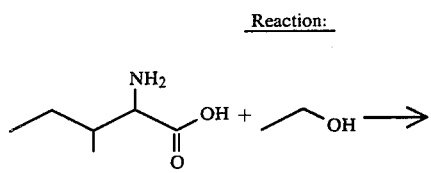

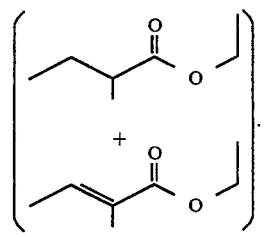

Into a 28 liter fermenter (working volume 22 liters) is added 22 liter of fermentation batch containing 110 grams isoleucine; 22 grams KH₂PO₄; 22 grams yeast extract; 11 grams MgSO₄.7H₂O; 1100 grams of 50% sterilized solution of dextrose.

The pH is adjusted to 6.5 and inoculum containing 1000 ml of a solution of *Geotrichum fragrans* (ATCC 11247) is added (the cell growth period is 3 days).

The pH is maintained in the range of 5 up to 5.5 using 5 molar potassium hydroxide solution. The foaming is controlled using silicone antifoam.

The aerate is 5 liters per minute per liter.

Ethanol is added to the reaction mass at the rate of 4 ml per hour maintaining the ethanol level in the range of 0.5% up to 0.875% (total ethanol added: 294 ml of 75% ethanol). Results: the first charcoal trap 352 on first extraction yielded 108.5 grams of ester containing 26.6% ethyl-2-methyl butyrate and 17.3% ethyl tiglate. The recycled charcoal yielded 7.48 grams of ester containing 18.8% ethyl-2-methyl butyrate and 15.9% ethyl tiglate. The second charcoal trap 353 contained 8.24 grams of ester containing 38.3% ethyl-2-methyl butyrate and 6.93% ethyl tiglate. On recycle 4.9 grams of ester yielded 39.7% ethyl-2-methyl butyrate and 1.7% ethyl tiglate. The first trap, second extraction yielded 7.89 grams ester containing 36.3% ethyl-2-methyl butyrate and 5.7% ethyl tiglate. The second trap on second extraction yielded 5.12 grams ester containing 39.7% ethyl-2-methyl butyrate and 3.12% ethyl tiglate.

In summary, a total of 63.1 grams ester was obtained containing the following:

| Distillate Component | Percentage |
|---|---|
| Ethyl methyl butyrate | 2.5 |
| Ethyl-2-methyl butyrate | 43.4 |
| Ethyl isovalerate | 16.2 |
| 2-Methyl-1-butanol | 2.9 |
| Ethyl tiglate | 32.0 |

EXAMPLE VII

PREPARATION OF ESTER MIXTURE

Reaction:

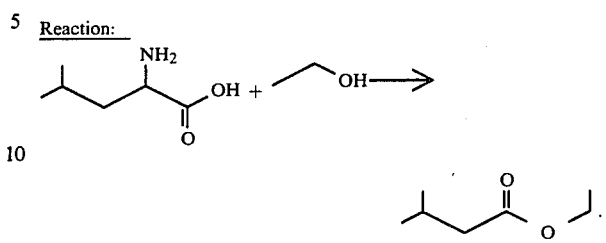

The same procedure was carried out as was carried out in Example VI with the following exceptions:
(i) leucine, rather than isoleucine, was used;
(ii) no antifoam was added;
(iii) the inoculum volume is 200 ml;
(iv) the pH is kept at 5; and
(v) the rpm for the agitation of the fermentation batch is 590 rpm.

The major product obtained is ethyl isovalerate with a minor amount of ethyl senecioate.

EXAMPLE VIII

PREPARATION OF ESTER MIXTURE

Reaction:

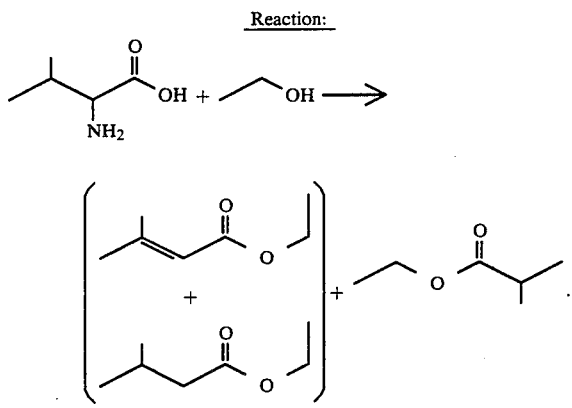

At 25° C. a 4.5% solution of *Geotrichum fragrans* (ATCC 24512) is grown over a period of 24 hours.

A fermentation batch is placed into the apparatus of FIG. 5 into fermenter 333 as follows:

| Ingredient | Percentage of Fermentation Batch |
|---|---|
| Valine | 4% |
| MgSO₄.7 H₂O | 0.05% |
| KH₂PO₄ | 0.1% |
| AMBEREX ® | 0.1% |
| CERELOSE ® | 4.5% |
| TWEEN ® 80 | 0.02% |

The fermentation is carried out over a period of 72 hours at the following conditions:

| | |
|---|---|
| Aeration level: | 0.73 liter/per/liter/per/minute |
| Agitation rate: | 400 rpm |
| Temperature: | 24–26° C. |
| pH range: | 5.00–5.10 |
| Total ethanol added: | 550 ml |
| Recovery | Propylene glycol |

| | |
|---|---|
| distillation liquid aid: | |

A total working volume of 22 liters in the fermentation batch is used.

A total of 74.5 grams of ester product was recovered from the charcoal traps having the following composition:

| | |
|---|---|
| Ethanol propionate: | 10.3% |
| Ethyl isobutyrate: | 37.0% |
| Ethyl isovalerate: | 28.1% |
| Ethyl tiglate: | 4.5% |

FIG. 13 is the GLC profile for the resulting ester mixture.

The peak indicated by reference numeral "1301" is the peak for ethanol. The peak indicated by reference numeral "1302" is the peak for ethyl propionate. The peak indicated by reference numeral "1303" is the peak for ethyl isobutyrate. The peak indicated by reference numeral "1304" is the peak for ethyl isovalerate and ethyl-2-methyl butyrate. The peak indicated by reference numeral "1305" is the peak for ethyl tiglate.

The ethyl tiglate is in the reaction mass because in the inoculum, a small amount of isoleucine was contained. The peak containing ethyl-2-methyl butyrate in addition to ethyl isovalerate contained ethyl-2-methyl butyrate because an isoleucine impurity was contained in the inoculum.

EXAMPLE IX

PREPARATION OF ESTER MIXTURE

Reaction:

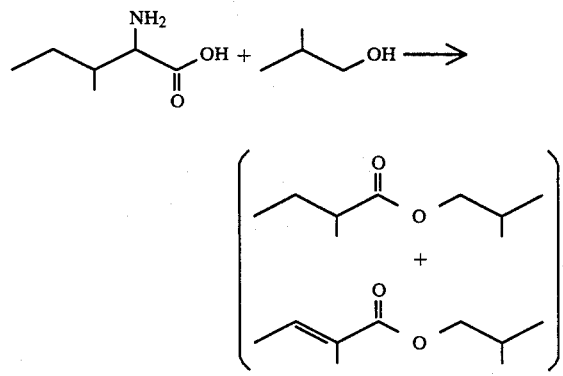

A procedure was carried out as in Example VIII with the following exceptions:

(i) 165 ml of isobutanol was used in place of ethanol; and (ii) the fermentation batch contained 0.45% isoleucine in place of the valine.

FIG. 14 is the GLC profile for the ester mixture thus produced.

The peak indicated by reference numeral "1401" is the peak for isobutyl propionate. The peak indicated by reference numeral "1402" is the peak for isobutyl isobutyrate. The peak indicated by reference numeral "1403" is the peak for isobutyl-2-methyl butyrate and isobutyl isovalerate. The peak indicated by reference numeral "1404" is the peak for isobutyl tiglate.

What is claimed is:

1. A process for producing esters defined according to the generic structure:

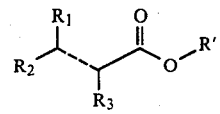

wherein $R_1$, $R_2$ and $R_3$ each represents methyl or hydrogen; wherein the dashed line represents a carbon-carbon single bond or a carbon-carbon double bond and wherein $R'$ represents $C_2$-$C_5$ alkyl comprising the step of reacting an amino acid having the structure:

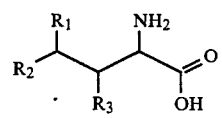

with a $C_2$-$C_5$ alkanol in the presence of the fermentation organism, *Geotrichum fragrans*, ATCC 11247, said reaction taking place by bubbling air through the reaction mass containing one or a mixture of amino acids defined according to the structures:

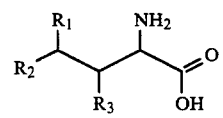

and a $C_2$-$C_5$ alkanol, said reaction taking place in the presence of a carbon source selected from the group consisting of:

Dextrose;
Maltose;
Lactose;
Fructose;
Sucrose;
Black strap molasses;
Corn syrup;
Corn syrup solids; and
Corn starch, the concentration range of the amino acids or mixture of amino acids varying from about 0.1% by weight of the total contents of the reaction mass up to about 1.0% by weight; the concentration of carbon source in the reaction mass varying from about 0.5% up to about 8.0%; the reaction taking place at a pH of from about 4.0 up to about 7.5 at a temperature of from about 20° C. up to about 35° C.; the time of fermentation varying from about 20 hours up to about 100 hours.

2. The process of claim 1 wherein the amino acid is leucine.

3. The process of claim 1 wherein the amino acid is valine.

4. The process of claim 1 wherein the amino acid is isoleucine.

5. The process of claim 1 wherein the reaction carried out is:

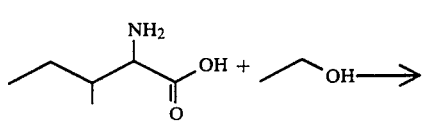
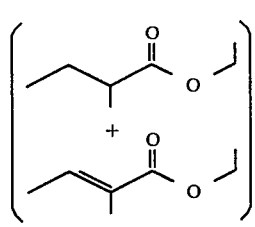
6. The process of claim 1 wherein the reaction carried out is:
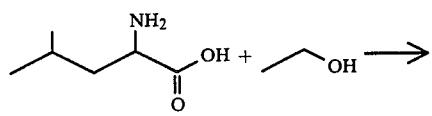
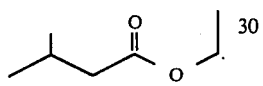
7. The process of claim 1 wherein the reaction carried out is:
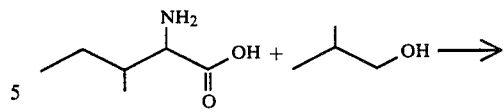
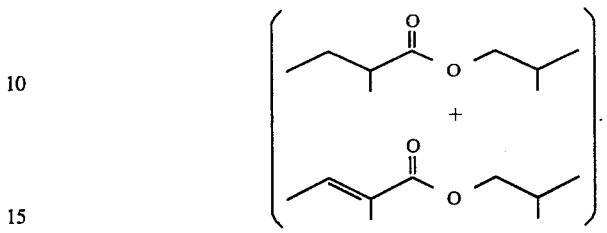
8. The process of claim 1 wherein the reaction carried out is:
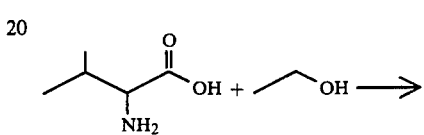
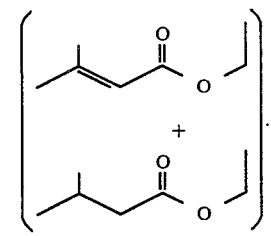
* * * * *